(12) United States Patent
Mathur et al.

(10) Patent No.: US 9,890,402 B2
(45) Date of Patent: Feb. 13, 2018

(54) THRAUSTOCHYTRID BASED PROCESS FOR TREATING WASTE EFFLUENTS

(71) Applicants: INDIAN OIL CORPORATION LIMITED, Mumbai (IN); DEPARTMENT OF BIOTECHNOLOGY, New Delhi (IN)

(72) Inventors: Anshu Shankar Mathur, Faridabad (IN); Dilip Singh, Faridabad (IN); Preeti Mehta, Faridabad (IN); Ravi Prakash Gupta, Faridabad (IN); Deepak Kumar Tuli, Faridabad (IN)

(73) Assignees: INDIAN OIL CORPORATION LIMITED, Mumbai (IN); DEPARTMENT OF BIOTECHNOLOGY, New Delhi (IN)

( * ) Notice: Subject to any disclaimer, the term of this patent is extended or adjusted under 35 U.S.C. 154(b) by 0 days.

(21) Appl. No.: 15/004,809

(22) Filed: Jan. 22, 2016

(65) Prior Publication Data
US 2016/0244789 A1    Aug. 25, 2016

(30) Foreign Application Priority Data
Jan. 24, 2015 (IN) .......................... 247/MUM/2015

(51) Int. Cl.
| | | |
|---|---|---|
| *C12N 1/00* | (2006.01) | |
| *C12P 7/64* | (2006.01) | |
| *C12R 1/90* | (2006.01) | |
| *C02F 3/28* | (2006.01) | |
| *C02F 3/34* | (2006.01) | |
| *C12N 1/10* | (2006.01) | |
| *C12N 1/12* | (2006.01) | |
| *C02F 101/10* | (2006.01) | |
| *C02F 103/06* | (2006.01) | |
| *C02F 103/18* | (2006.01) | |

(52) U.S. Cl.
CPC .............. *C12P 7/6427* (2013.01); *C02F 3/28* (2013.01); *C02F 3/348* (2013.01); *C12N 1/10* (2013.01); *C12N 1/12* (2013.01); *C12P 7/649* (2013.01); *C12P 7/6463* (2013.01); *C12P 7/6472* (2013.01); *C12R 1/90* (2013.01); *C02F 2101/101* (2013.01); *C02F 2103/06* (2013.01); *C02F 2103/18* (2013.01); *Y02E 50/13* (2013.01)

(58) Field of Classification Search
None
See application file for complete search history.

(56) References Cited

U.S. PATENT DOCUMENTS

| | | |
|---|---|---|
| 5,130,242 A | 7/1992 | Barclay |
| 5,340,742 A | 8/1994 | Barclay |
| 6,582,941 B1 | 6/2003 | Yokochi et al. |
| 6,607,900 B2 | 8/2003 | Bailey et al. |
| 7,989,195 B2 * | 8/2011 | Chi ................. C12P 7/6409 435/257.1 |
| 2009/0117194 A1 | 5/2009 | Burja et al. |
| 2010/0041112 A1 | 2/2010 | Fisher et al. |
| 2012/0198758 A1 | 8/2012 | Schideman et al. |
| 2013/0065282 A1 | 3/2013 | Tran et al. |
| 2013/0089901 A1 | 4/2013 | Seo et al. |
| 2013/0217084 A1 | 8/2013 | Wen |

FOREIGN PATENT DOCUMENTS

WO    2007068997 A2    6/2007

OTHER PUBLICATIONS

Jasuja et al. Pharmacologyonline, 2009, 2, pp. 341-349.*
Harel et al. FEMS Microbiol. Ecol., 2008, 64, pp. 378-387.*
Rao et al. Clean Techn Environ Policy. 2003, pp. 66-71.*
Chisti et al "Biodiesel from microalgae" Biotechnology Advances 2007.
"Global market for EPA/DHA Omega-3 Products," Packaged Facts Sep. 2012.

* cited by examiner

*Primary Examiner* — Vera Afremova
(74) *Attorney, Agent, or Firm* — Maschoff Brennan

(57) ABSTRACT

The present invention relates to the continuous process of sequestration of nutrients from waste effluents released from gas fermentation plants or green-house gases emission managing plants by novel Thraustochytrids. Particularly this invention relates to the methods and systems to enhance sequestration rate and productivity of the process. This invention also relates to rapid biotransformation of nutrients present in waste effluents into high value omega-3 fatty acids like Docosahexaenoic acid (DHA), Docosapentaenoic acid (DPA), Eicosapentaenoic acid (EPA) and lipids for biodiesel. This disclosure is about means of processing of waste streams and producing value added products out of it.

17 Claims, 10 Drawing Sheets

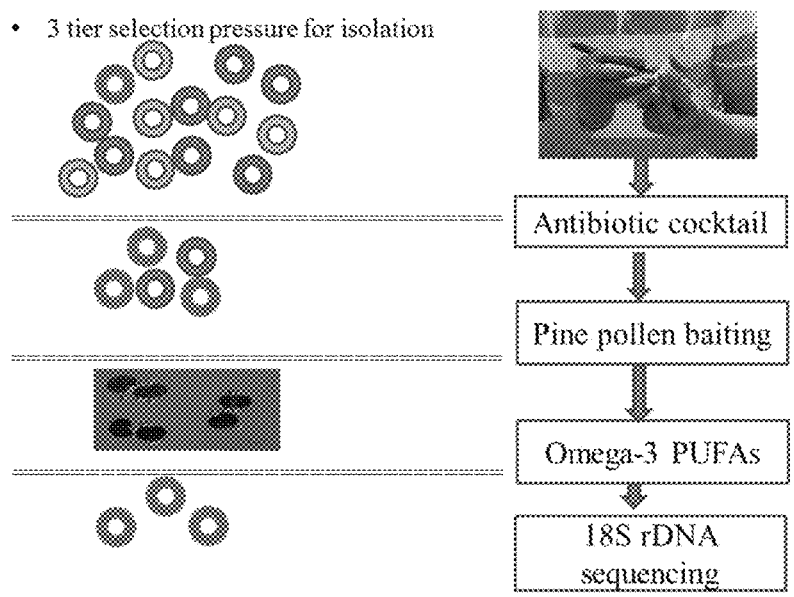
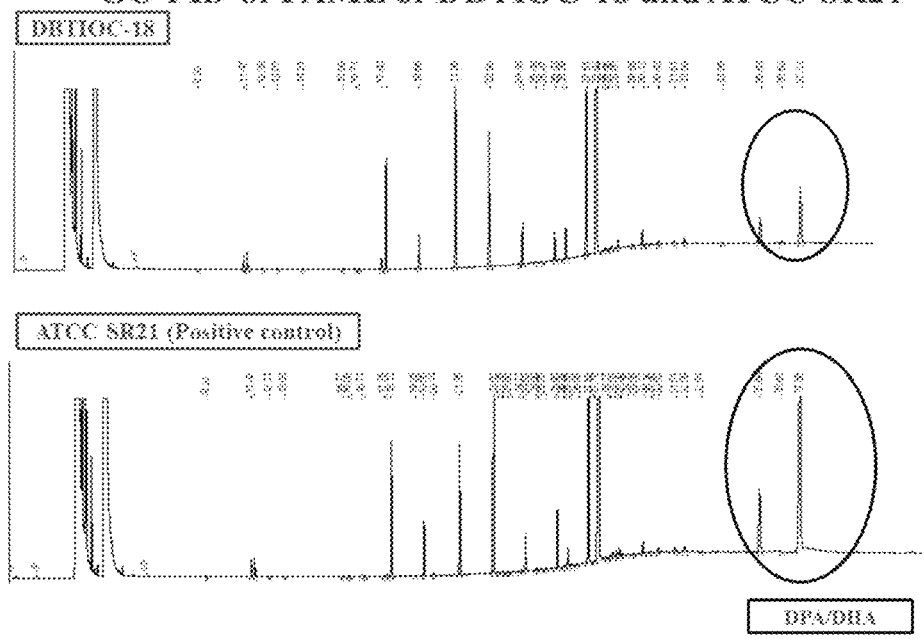
Figure 1: Strategy employed for the *Thraustochytrid* isolation

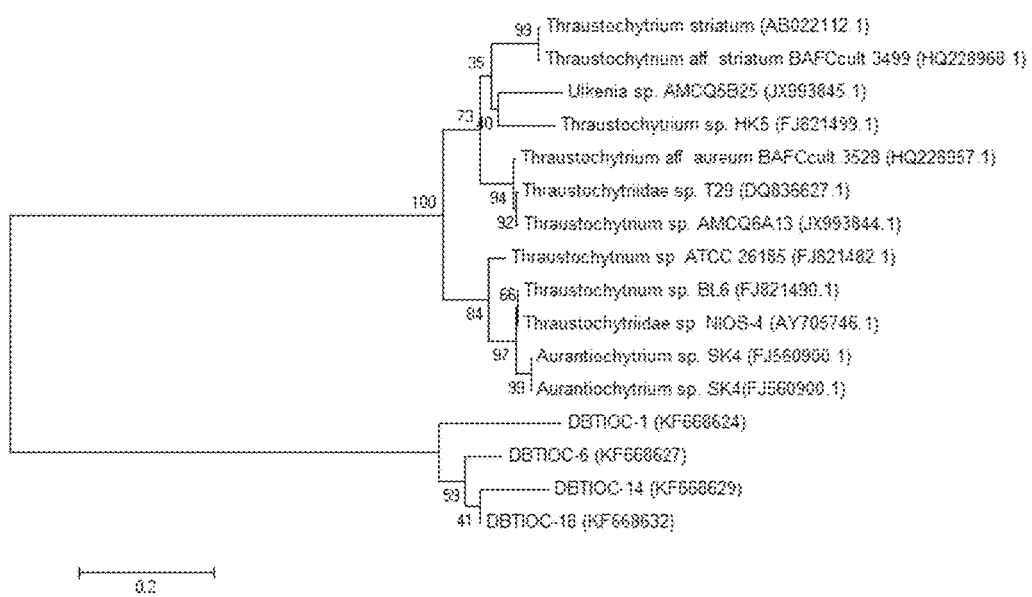
Figure 2. Phylogenetic relationship (NJ tree) of novel *Thraustochytrid* strains with existing *Thraustochytrids*

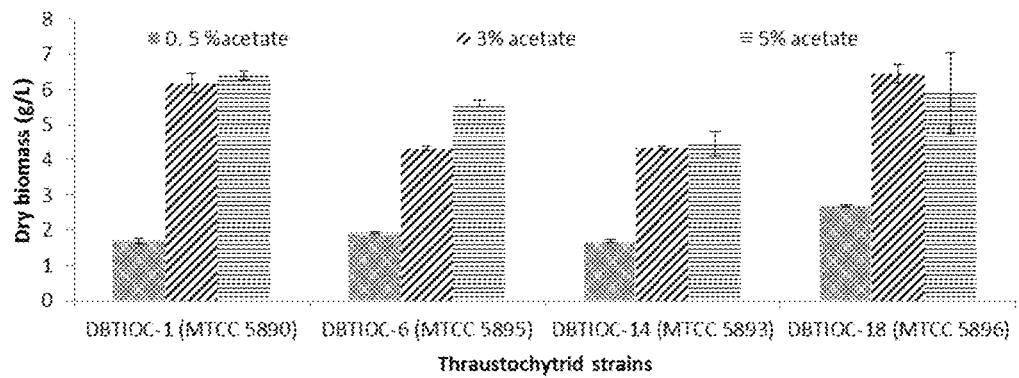
Figure 3(a). Acetate tolerance and biomass production on different concentration of acetate by *Thraustochytrid* strains
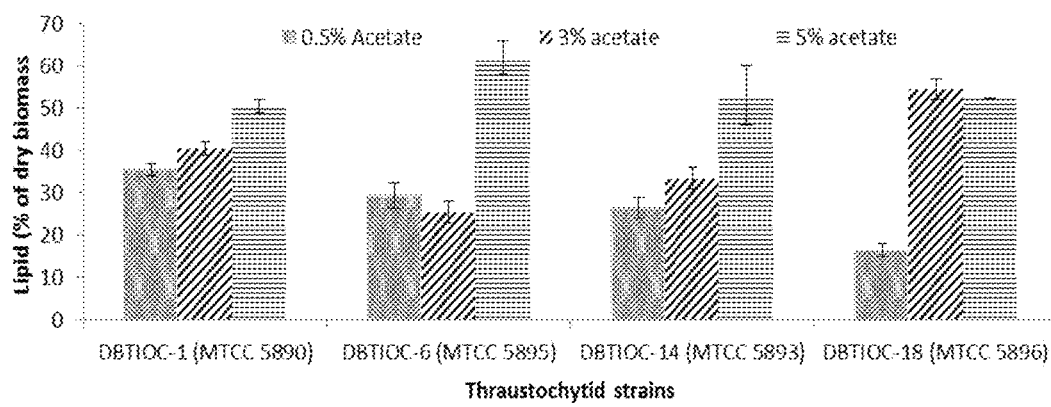
Figure 3(b). Acetate tolerance and lipid content on different concentration of acetate by *Thraustochytrid* strains

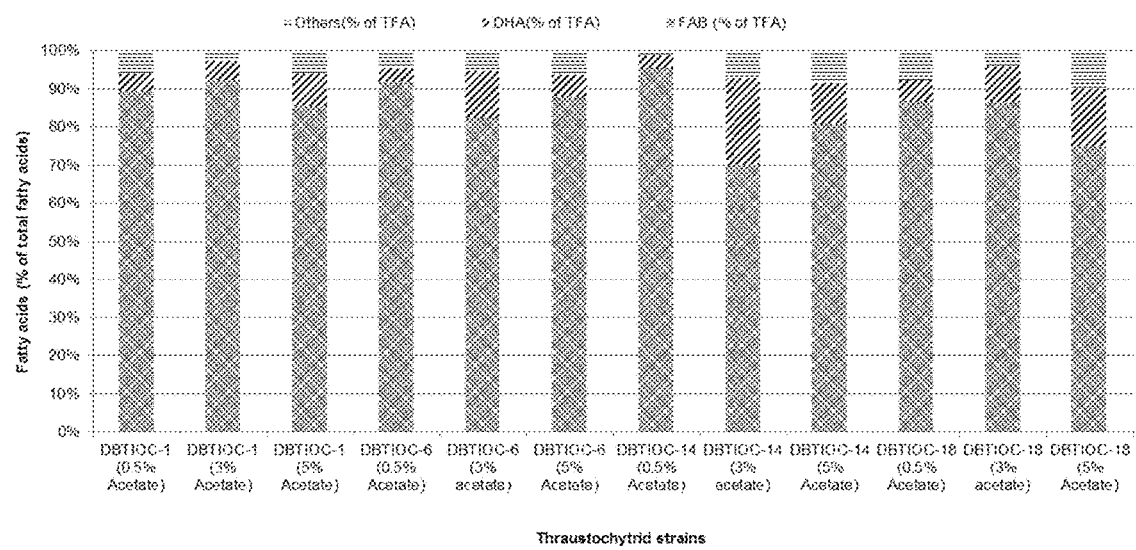
Figure 3(c). FAB and DHA content on different concentration of acetate by *Thraustochytrid* strains
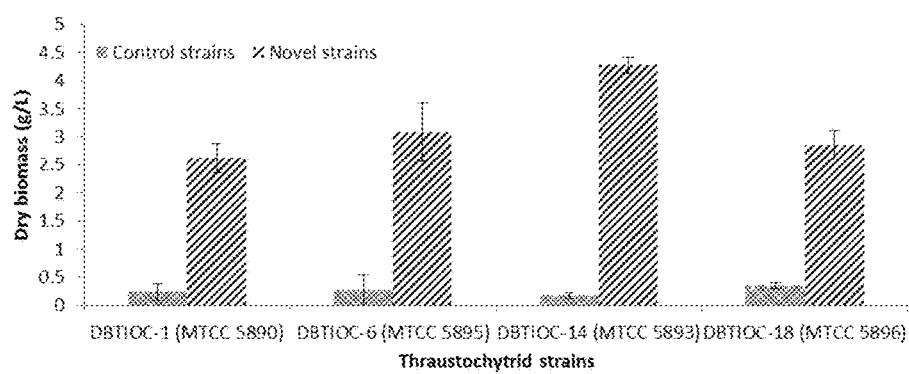
Figure 4(a). Biomass production of *Thraustochytrid* strains on waste effluents

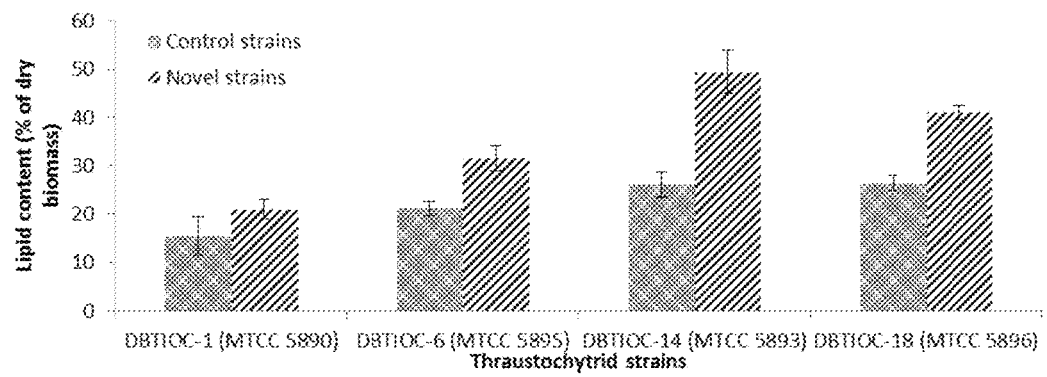
Figure (4b). Lipid content of *Thraustochytrid* strains on waste effluents
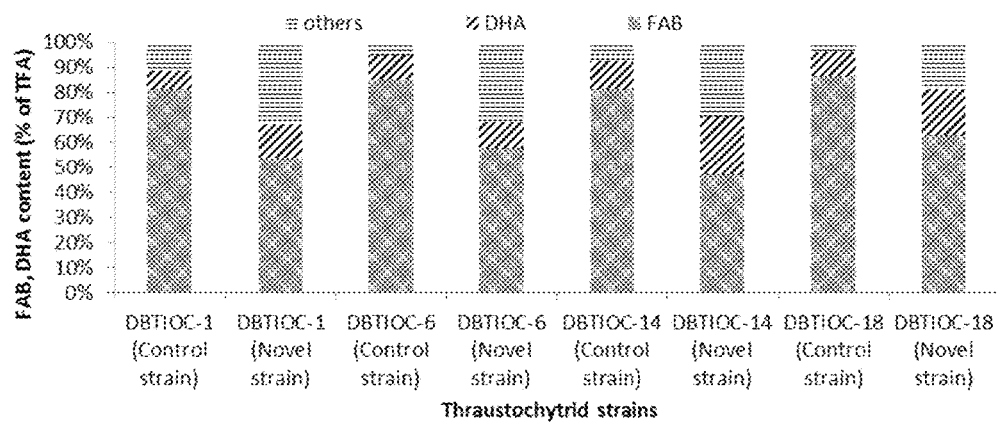
Figure 4(c). FAB and DHA content of *Thraustochytrid* strains on waste effluents

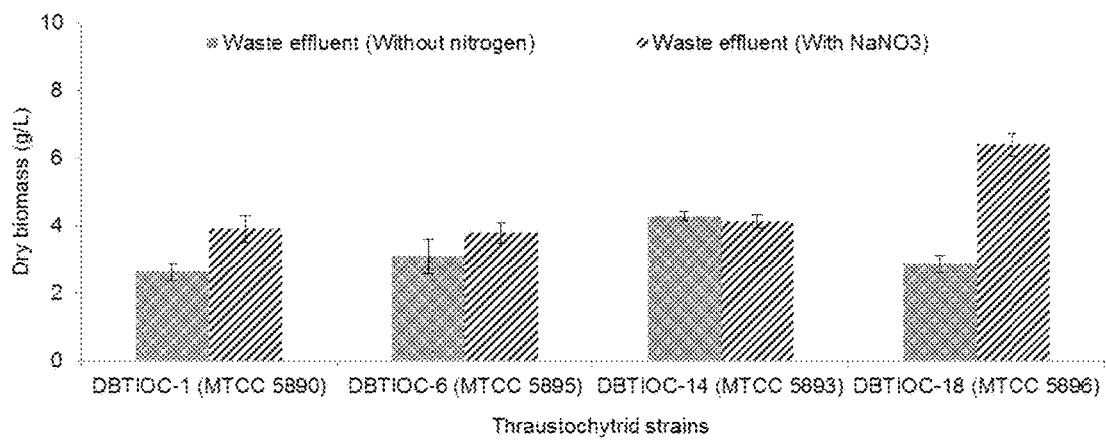
Figure 5. Effect of addition of nitrogen source on biomass production on waste effluent stream
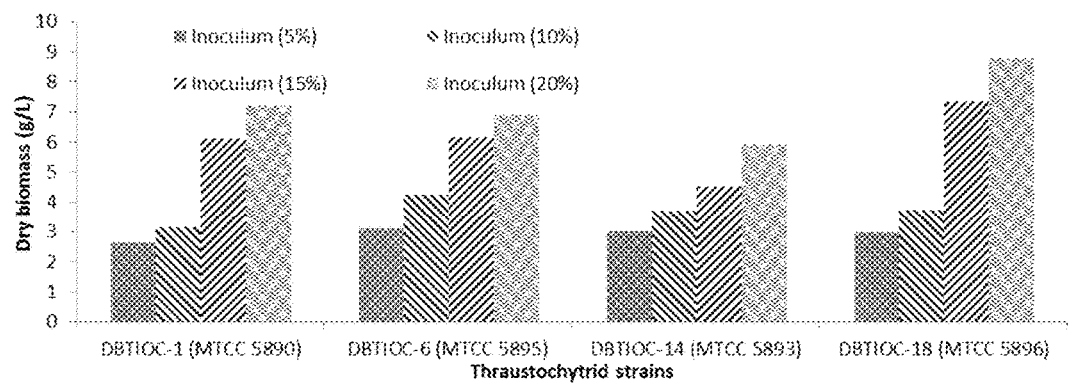
Figure 6. Effect of different inoculum sizes on biomass production on waste effluent stream

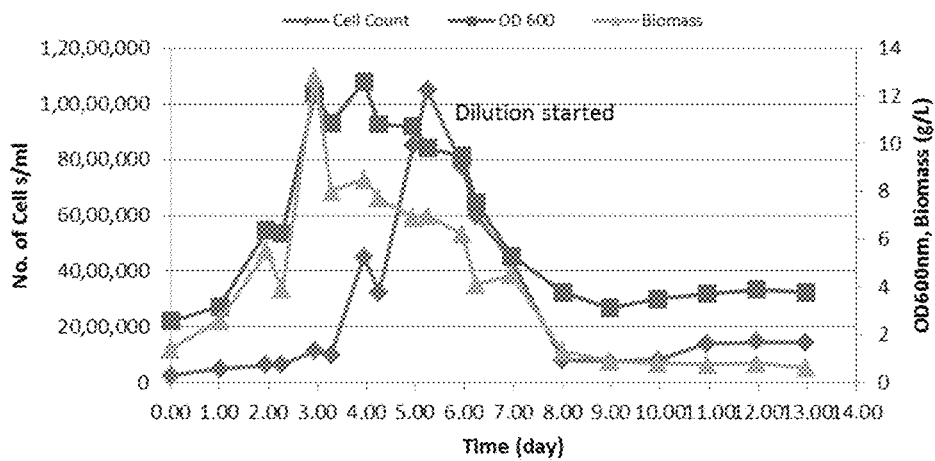
Figure 7(a). Cell count, Cell $OD_{600nm}$, dry biomass in bioreactor with combination of Rushton impeller and drilled pipe spargers for the cultivation of DBTIOC-18 (MTCC 5896) on waste effluent stream
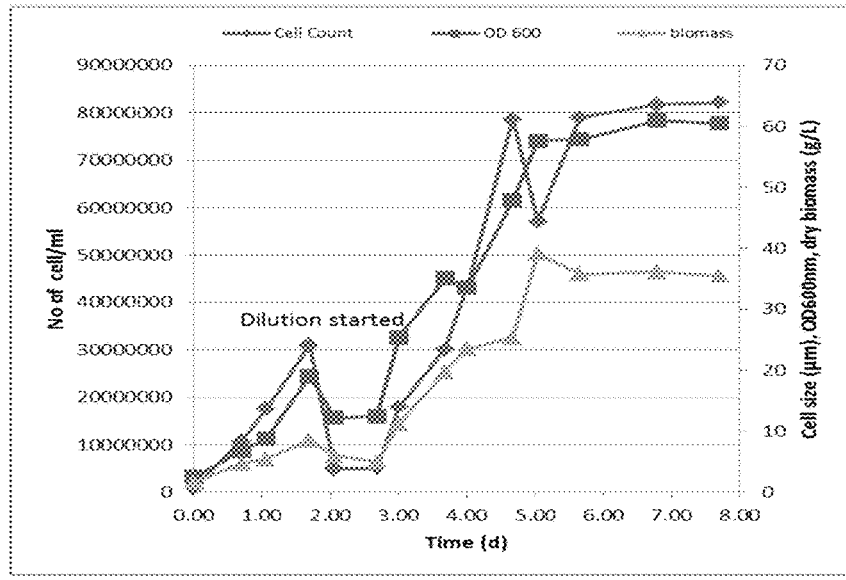
Figure 7(b). Cell count, Cell $OD_{600nm}$, dry biomass in bioreactor with combination of pitch blade and microspargers for the cultivation of DBTIOC-18 (MTCC 5896) on waste effluent stream

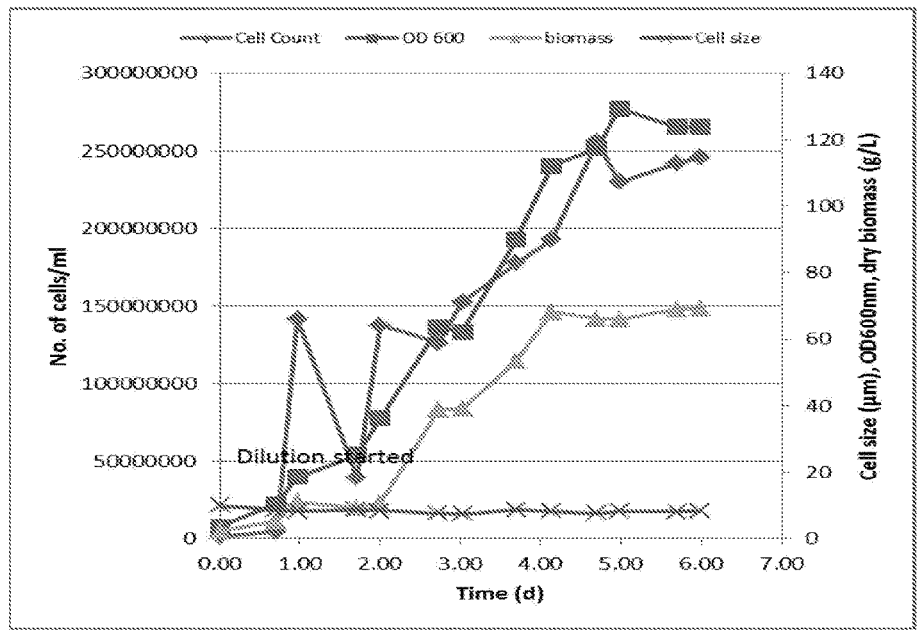

Figure 8. Cell count, cell OD$_{600nm}$, cell size, dry biomass in bioreactor with combination of pitch blade and microspargers for the cultivation of DBTIOC-18 (MTCC 5896) on waste effluent stream continuously purged with air.

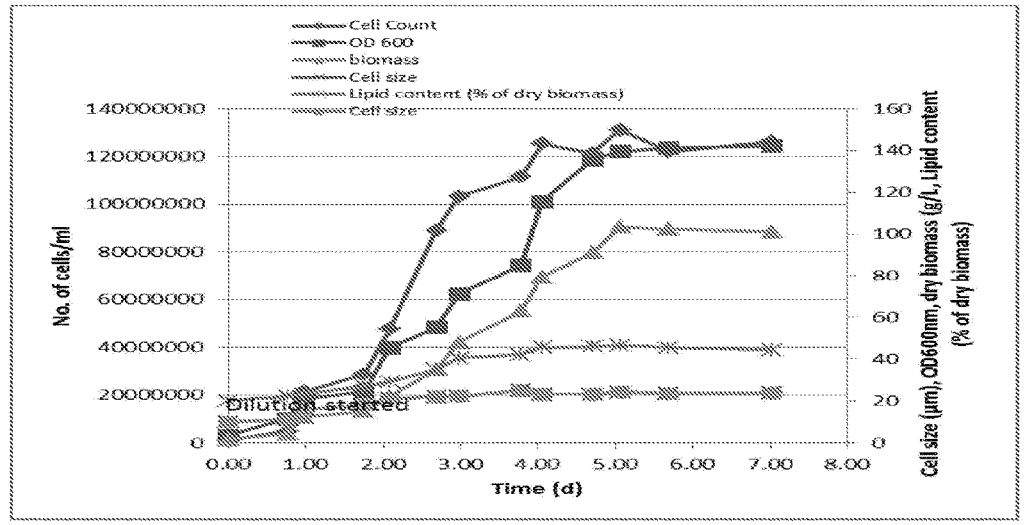

Figure 9. Cell count, cell OD$_{600nm}$, cell size, dry biomass and lipid content in two stage bioreactor system, First reactor was continuously supplied with waste stream having nitrogen source whereas second reactor was supplied waste streams without amending with nitrogen source for the cultivation of DBTIOC-18 (MTCC 5896)

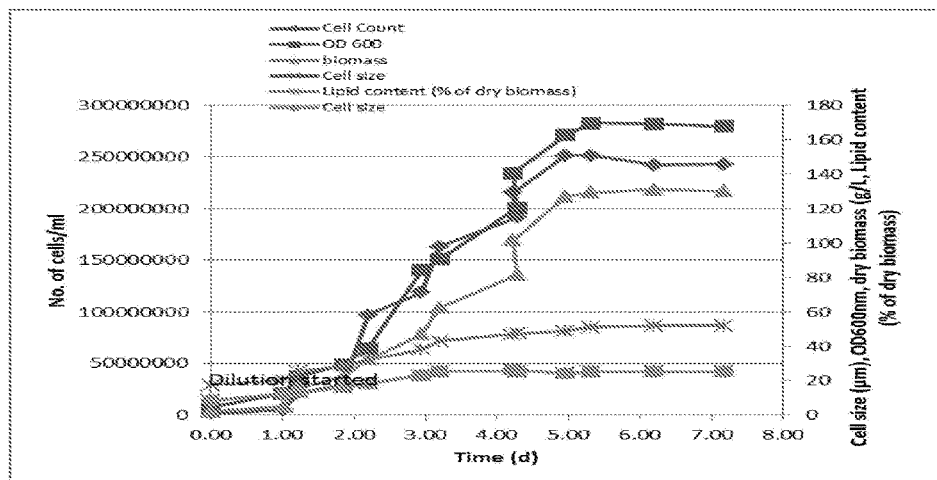

Figure 10. Cell count, cell $OD_{600nm}$, cell size, dry biomass and lipid content in two stage bioreactor system with inline biomass harvesting system, First reactor was continuously supplied with waste stream having nitrogen source whereas second reactor was supplied waste streams without amending with nitrogen source for the cultivation of DBTIOC-18 (MTCC 5896). Biomass was continuously concentrated from broth coming out of first reactor and concentrated biomass was continuously pumped into second reactor.

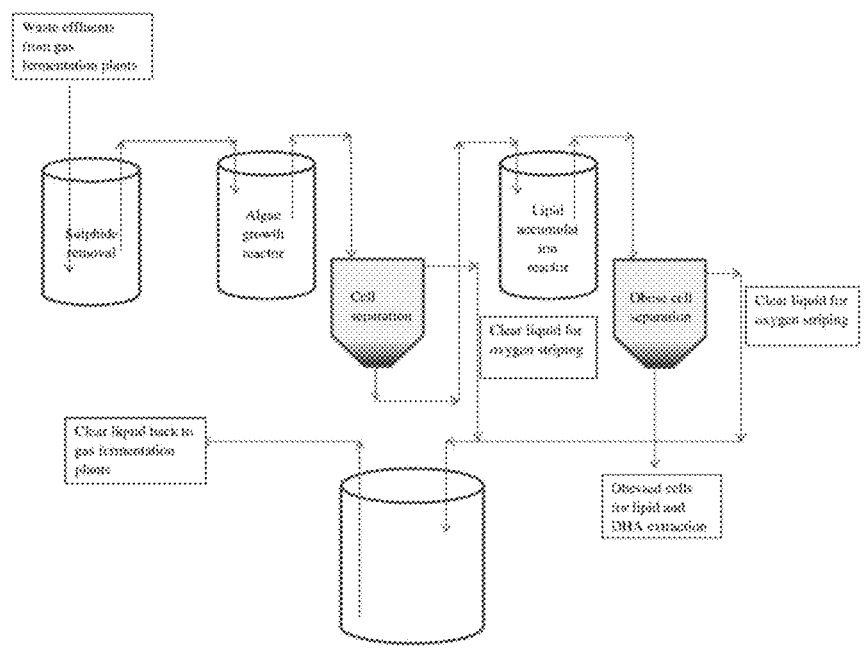
Figure 11. Schematic diagram of the process for the conversion of waste effluents to lipid and DHA

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Forward Primer Sequence

<400> SEQUENCE: 1
caacctggtt gatcctgcca gta                                              23

<210> SEQ ID NO 2
<211> LENGTH: 24
<212> TYPE: DNA
<213> ORGANISM: Artificial Sequence
```

```
<220> FEATURE:
<223> OTHER INFORMATION: Reverse Primer Sequence

<400> SEQUENCE: 2
tcactacgga aaccttgtta cgac                                        24
```

THRAUSTOCHYTRID BASED PROCESS FOR TREATING WASTE EFFLUENTS

FIELD OF INVENTION

The present invention provides for thraustochytrid based process for treating waste effluents in a continuous process of sequestration of nutrients from discharge of gas fermentation plants and its biotransformation in value added products such as high value omega-3 fatty acids and lipids for biodiesel The sequence listing disclosed herein is included in a text file having the name "sequence.txt," created on May 12, 2016, having a size of 730 bytes. The foregoing text file is incorporated herein by reference.

BACKGROUND

Rapid industrialization in the developing countries although brought economic development but also severely degraded ecosystems of Earth such as water and soil especially by discharge coming out of the industries. This has highlighted the need for efficient processing of waste effluents discharged from the industries to prevent the degradation of ecosystems of earth. With the maturity of upcoming technologies for biofuel production for example carbon capture and sequestration technologies, gas fermentation of green-house gases, bioethanol production from lignocellulosic biomass and pyrolysis of lignocellulosic biomass, large amount of waste effluent streams are expected to be generated thus exaggerating the existing problem. Most of the effluents from biofuel industry contain large amount of organic acids, alcohols (for example formic acid, acetic acid, butyric acid, methanol and ethanol) and sugar derivatives etc. Disposing these effluents directly in environment without treatment may further impact the biodiversity of the area since these acids and alcohol are highly corrosive and toxic to living beings. Therefore these effluents must be treated chemically and biologically before discharging in environment.

Treatment of these effluent streams chemically or biologically incurs significant cost to industries thus hurting their profits however producing useful materials out of these effluents may add credit to the processes. Organic acids/alcohol particularly acetic acid are precursor of various chemicals of industrial use however extracting these from these waste effluents is commercially unsustainable due to the comparatively lower amount present in these streams and higher cost and energy footprint associated with it. These types of effluents however can be used as sources of nutrients for growth of microorganisms especially microalgae for bioproduct generation and utilization. This will not only solve the problem of processing of waste effluents but also cheap and sustainable supply of nutrient source for the cultivation of microalgae. This will add value and synergy to both the processes. However screening of microorganisms has to be done on these effluent streams since not all the microorganisms can utilize relatively higher concentration of organic acids and higher concentration of acetic acid/alcohol is reported to negatively impact growth of microbes.

Most of the natural microorganisms/microalgae are unable to tolerate or utilize higher concentration of organic acids and alcohol (particularly formic acid, acetic acid and ethanol) in the media. Therefore physiology of these microbes needs to be altered to enhance the tolerance and utilization of these nutrients in media. Genetic engineering, mutation, adaptation, protoplast fusion are such example of tools, which is being used to alter the physiology of the microbes to suit the desired application.

Most of the microalgae have ability to produce lipids in a heterotrophic mode utilizing broad range of nutrients. Heterotrophic cultivation of microalgae offers several advantages over the phototrophic cultivation like better control of culture parameters, high cell biomass and growth rate, high lipid accumulation up to 70-80% of cell dry weight in a short time. Some microalgae species such as Thraustochytrids can also produce omega-3 fatty acids i.e. DHA, DPA and EPA in significant amount along with lipids. These microorganisms can utilize broad spectrum of carbon and nitrogen source making them ideal for the economical production of both i.e. omega-3 fatty acids and biodiesel.

Most of the gas fermentation plants capturing green-house gases from different industrial sources are operated continuously instead of batch or fed batch mode. Therefore process for sequestration of nutrients from discharge of gas fermentation plants needs to be operated continuously instead of commonly used batch of fed batch process. This will not only help to synchronize gas fermentation process with nutrient sequestration process but also reduces operating cost and enhance productivity of the later process.

In continuous process, nutrients including nitrogen source are continuously supplied to the reactor, which will result into higher growth but low lipid accumulation. However oleaginous microorganisms are reported to accumulate lipid under nitrogen stress conditions. Nitrogen stress catalyses conversion of excess carbon source into lipid accumulation once nitrogen is completely consumed in the media, therefore higher carbon to nitrogen ratio is required for higher lipid production in batch or fed batch mode of cultivation. In continuous process, higher carbon to nitrogen ratio may result into higher lipid accumulation but low growth, which will translate into lower productivity of biomass, lipid and omega-3 fatty acids.

To overcome this issue, two reactors systems are applied where one reactor is meant to support higher growth and second reactor is meant for lipid accumulation under nitrogen stress conditions. However these two reactors are operated in separate batch instead of continuous mode Culture broth from first bioreactor is directly transferred to second bioreactor however this conventional approach possess numerous challenges for example (i) dilution of media components in second reactor by culture broth from first reactor, (ii) reduced biomass and lipid productivity due to drop in number of cell per ml in second reactor, (iii) chances of nitrogen contamination in second reactor caused by unutilized nitrogen present in culture broth coming from first reactor, (iv) subsequent accumulation of secondary metabolites in second reactor, which are detrimental for lipid accumulation Based on the sources of feedstock, biodiesel has been classified into first generation, second generation, and third generation biodiesel. First generation biodiesel are being commercially produced from edible crops (e.g. Soybean Canola oil, palm oil etc.) but the viability of the first generation biodiesel in long term is however questionable because of the conflict with food supply and hence the Food vs. Fuel debate. Second generation (Non edible crops e.g. karanja oil, jatropha etc.) could be the answer for this demand but lack of adequate productivity, higher investment on water and fertilizers, vast areas of land for commercial production made limited exploiting for commercial purpose.

However, third generation biodiesel, which is derived from microbial biomass, has emerged as front runner to address the feedstock problem because of their high growth rate and oil productivity as compared to bioenergy crops. Such microorganisms belong to Yeast and Microalgae and are designated as oleaginous microorganisms, if they accumulate more than 20% of their dry weight as lipids. Oil productivity of these oleaginous microorganisms exceeds almost thousand times over superior oil crops such as palm, soybean, coconut etc and the land area needed for large scale production is far lower than oil crops (Chisti et al 2007 Biotechnology Advances). Thus cultivation of oleaginous microorganism for biodiesel application gives a commercial and sustainable edge over oil crops.

Commercial success of microalgal biodiesel depends on its cost competitiveness as compare to fossil derived fuels. The requirements for economically viable production of oil include factors such as high biomass and lipid productivity, low cost of raw material and co-product credit. A review of the microalgal biofuel indicates that cultivation of species only giving lipids for biodiesel production is not economical. The reasons include higher cultivation and nutrient cost coupled with cost associated with harvesting and oil extraction. Therefore, microalgae species which can provide value added products along with lipids are in high demand to offset some of the cost. Concurrent production of oil suited for biodiesel application and high value co-products such as DHA/DPA/EPA is one of the promising processes in order to offset the production cost thus giving leverage to biodiesel for competing against well-established petro diesel. However, selection of the good microalgae strains which can provide significant amounts of DHA/EPA/DPA remains one of the critical aspects for success of this technology.

Polyunsaturated fatty acids (PUFAs) viz. Docosahexaenoic acid (DHA), Docosapentaenoic acid (DPA) or Eicosapentaenoic acid (DPA) are the essential fatty acids and well documented for their important physiological roles in development of normal vision in infants, maintenance of brain functions, ocular tissues, heart muscles and inhibitor of macular degeneration in old people etc. Based on position of first double from end of carbon chain, PUFAs has been categorized in two class i.e. Omega-3 and omega-6 fatty acids, depend of presence of first double bond on alkyl chain opposite to carboxyl group. Broad spectrum importance of DHA in human physiology has made the companies dealing with infant food to formulate food supplement enriched with DHA, For example DHA accounts for approximately 15%-20% of lipids in the human cerebral cortex, which can be used as bio marker for analyzing the brain functioning of a particular individual, 30%-60% of lipids in the retina and is an important component of breast milk. These fatty acids are reported to have anti-inflammatory activities as well as ability to lower down blood cholesterol level. Regular dozes of DHA can be helpful to prevent the atherosclerosis by reducing the risk of blood vessel hardening. Recently it was reported that long term use of DHA can be helpful to reduce the chance of type-1 diabetes, non-alcoholic fat liver diseases and cancer by inducing apoptosis in cancerous cells. DHA application in cosmetics is reported to have anti-aging effect. Because omega-3 fatty acids are not synthesized de novo in the human body, these fatty acids must be derived from nutritional sources.

The broad spectrum of physiological importance, DHA/EPA is drawing significant attention from pharmaceutical industry, neutraceutical industry, poultry, and fisheries. Recently attempts have been made to expand DHA application in functional and health foods. World Health Organization (WHO) has suggested the daily intake of 1 g/day DHA for healthy persons. Due to their expanding application in various industries, market value for these omega-3 products is projected to be around US $35 billion by 2016 with compound annual growth rate of 6.8% from 2011-2016 (Global market for EPA/DHA Omega-3 Products, Packaged Facts 2012).

Fish oil is considered good dietary sources of omega-3 fatty acids. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants and can be associated with stability problems and a fishy odor or taste. Apart from this, Overfishing has also led to the faltering fish oil supply which forced the major producers such as DSM to increase the market price for DHA due to cost escalation in fish oil procurement.

These limiting issues with fish oil supply have forced the industries to look for alternative resources such as marine microalgae like Thraustochytrids, Crypthecodinum, or diatoms Phaeodactylum for DHA/EPA production in last two decades. Significant amount of research has been conducted for isolation of omega-3 oil producing marine microalgae. Thraustochytrids are deemed as one of the potential candidates for DHA production. Thraustochytrids are unicellular marine micro-heterotroph, associated with the degrading organic materials such as mangroves leaves, sediment and recycling of nutrients in mangrove ecosystem. Cell size ranges between 10-35 µm and reproduce through zoospores or binary fission. They act as decomposer in mangrove ecosystem. Based on molecular phylogeny, Thraustochytrids are classified in the Kingdom Chromista or Stramenipila (also called Stramenopila), alongside brown algae, diatoms, oomycetes and a variety of flagellates. While most of the members of this kingdom are saprophytic such as Thraustochytrids, some are the parasitic like member of labyrinthulids. High Biomass and Lipid production including DHA/EPA is well known to be produced by microalgae belongs to Thraustochytrids in nature. Thraustochytrids are microorganisms of the order Thraustochytriales and include members of the genus *Schizochytrium, Thraustochytrium, Ulkenia* and have been well established as an alternative source of omega-3 fatty acids, including DHA Out of total lipid present in thraustochytrid biomass, about 90%-95% is stored as triacyl glycerols (TAGs) followed by 5%-10% as polar and structural lipids (Gupta et al 2012 Biotechnology Advances). Saturated fatty acids (SFAs) such as Myristic acid (C14:0), Palmitic acid (C16:0) or mono unsaturated fatty acids e.g. Oleic acid (C18:1) and polyunsaturated fatty acids (PUFAs) like DHA (C22:6n3) are the major component of TAGs. SFAs and MUFAs constitute about 40%-80% of total fatty acids (TFAs) which are ideal fatty acids for biodiesel production (FABs). DHA constitutes 20%-50% of TFA. In last two decades, most of the research done for the development of Thraustochytrids is for development of a novel source of DHA production. Literature suggests that high biomass production (200 g/L) with high lipid accumulation (SFAs and MUFAs) makes them potential candidate for the concurrent production of biodiesel and high value co-products.

Thraustochytrids are well documented for their ability to produce high amount of biomass and lipid coupled with DHA/EPA production using variety of carbon and nitrogen sources. However source of carbon and nitrogen supply whose costs also impacts the overall production economics has to be carefully chosen. Glycerol, crude glycerol, coconut water, soybean meal and sweet sorghum juice are few examples of cheap nutrients. Glycerol especially crude glycerol from biodiesel industry has been aggressively advocated as alternative of glucose for the Thraustochytrid cultivation by researchers. However with the shifting of focus of biodiesel industry from non-edible oil to microalgal oil as feedstock of biodiesel, supply and cost dynamics of crude glycerol would also change resulting into drop in carbon source supply for Thraustochytrid cultivation. It has been observed that the cost of the carbon source is a single most significant factor for overall economics of lipid/DHA production.

Thraustochytrids are exclusively marine microbes, cultivated in media having sea water or sea salt. There are some reports suggesting the replacement of sea water or sea salt with sodium chloride or sodium sulphate. However addition of sea salt, sea water, sodium chloride and sodium sulphate are reported to corrode the walls of commercial scale reactors in long term operations. Thus media formulations without the inclusion of sea salt, sea water, sodium chloride and sodium sulphate will have multiple advantages for example easier maintenance of reactors, reduced likelihoods of corrosive metal contamination in media, monetary benefits in maintenance of reactors and media preparations.

Patent publication number US 2013/0065282 describes the process of anaerobic fermentation of green-house gases such as carbon dioxide along with hydrogen into ethanol and acids. This stream was later used as carbon source for the production of lipids by oleaginous yeasts for example *Cryptococcus curvatus*. It is disclosed in this that 1.5% w/v acetate was used in the media for the cultivation since use of more than 1 to 1.5% of acetate is reported to negatively affect the growth. Therefore waste effluent streams containing more than 1.5% of acetate may restrict the growth of these oleaginous yeasts. Author claimed lipid productivity of 20 g/L/d but lipid content remained very low in dry biomass of the said yeast. Dry biomass of this yeast also lack of any highly valuable product which may discourage the industry to employ this platform for processing of waste effluents.

US patent application number US 2012/0198758 A1 discusses the conversion of municipal sewage stream into bio crude oil by employing hydrothermal process on wet algal biomass and biosolid fraction of municipal waste. The used stream was mentioned to be rich in human waste, food waste, and pharmaceutical waste or used water supply of community. The process involved heating of solid fraction, wet biomass of algae and bacteria at very high temperature and pressure for the conversion into biocrude oil. Although this process eliminated the need of biomass drying, selection of high oil content microorganisms but energy required to carry out hydrothermal process was higher than the energy content of the biocrude oil. Apart from that any high value coproduct extractable from algal biomass will be also denatured at such harsh conditions of hydrothermal reactor, thus reducing the possibility of coproduct credit during the conversion of municipal waste to biocrude oil, which will in turn dampen the industries to adopt such technologies for processing their waste effluents. However processes converting these waste effluents into biodiesel and high value products such as DHA will be of significant interest.

U.S. Pat. No. 5,130,242 (1992) describes the process for heterotrophic cultivation of microalgae which can be used for extracting omega-3 fatty acids. Claimants of the patent describes about the isolation of a fast growing Thraustochytrids and its subsequent cultivation on glucose or other sugars such as maltose, sucrose or starch for enhancing DHA content in the cell. A two stage fermentation strategy was employed in this patent, where first stage was exponential growth phase followed by lipid accumulation phase under nitrogen stress conditions. Authors also described the process of low temperature crystallization for separation and purification of omega-3 fatty acids from rest of the lipid and effect of sodium ion concentration on fatty acid accumulation. The whole cell extract of Thraustochytrids was later suggested to be used in the foods for nutritional supplement or fish or animal feed to enhance omega-3 content in the product derived from these industries for example fish oil, eggs etc. However, use of glucose or other commoditized carbon and nitrogen sources will not only escalate the production cost but also poses challenging question for long term supply of these commodities along with raising the commodity prices.

U.S. Pat. No. 6,582,941 B1 (2003) describes the isolation of fast growing thraustochytrid strains belonging to the species similar to *Schizochytrium limacinum* SR21. Claimants studied this strain to develop the process for producing lipid having omega-3 and omega-6 fatty acids in substantial percentage using glucose or glycerol as carbon source and ammonium salts along with corn steep liquor as nitrogen sources. Later they optimized the growth of this newly isolated strain *Schizochytrium limacinum* SR21 to enhance omega-3 and omega-6 fatty acids content. Different media formulations of carbon and nitrogen sources were tried to increase DHA production in the fermentation. However the choice of carbon source as glucose or glycerol may makes this process rather uneconomical and non-sustainable.

U.S. Pat. No. 6,607,900 mentions the process for high cell density cultivation of *Schizochytrium* strain with biomass from 17 g/L to 200 g/L with significant amount of lipid accumulation using glucose as carbon source. Patent claimed DHA content around 20%-25% w/w of total lipid. Stepwise aeration strategy was applied in this patent with high aeration rate at growth phase followed by low aeration rate at lipid accumulation phase once the nitrogen source i.e. ammonium hydroxide is totally consumed in the medium.

US 20090117194 describes the process for concurrent production of DHA with antioxidant production with novel thraustochytrid strain ONC-T18, which claimants isolated from Canadian marine biodiversity. 18S rDNA gene sequence of this isolate revealed its proximity with *Thraustochytrium striatum* T91-6. They used different concentration of glucose, monosodium glutamate and yeast extract to enhance biomass and DHA content in the cell. After trying several media formulations they reported substantial increase in biomass and lipid content up to 28.0 g L-1 biomass, 81.7% TFA and 31.4% DHA (w/w biomass).

U.S. Pat. No. 7,989,195 describes the process to achieve high cell density cultivation of *Schizochytrium limacinum* SR21 using crude glycerol as carbon source. Claimants present multiphase strategy dividing the whole fermentation in three phase i.e. increasing cell density, cell size and subsequent increase in fatty acid production. They claimed biomass productivity of 1 g/L/h to 3 g/L/h with 15%-22% DHA of total fatty acids. The crude glycerol used in this process was derived from biodiesel industry. Authors did not mention the effect of shearing on lipid accumulation since obese cells are very delicate and prone to cell damage due to shearing thus effect of shearing has to be taken into account while enhancing the lipid accumulation in the cell.

A US Patent application number 2013/0217084 A1 describes a process for DHA production from various thraustochytrid species i.e. *Schizochytrium, Thraustochytrium, Ulkenia* etc. using crude glycerol, generated from biodiesel industry, as carbon source. Claimants also studied EPA production in these species on crude glycerol. They mentioned about the value addition to biodiesel industry by converting acetate containing glycerol in to high value products.

Patent publication number US 2013/0089901 describes that the microalgae of the invention accumulate bio-oil at a high ratio in the cells when being cultured in glucose-containing medium, and thus can produce bio-oil in a high yield. The microalgae can produce bio-oil using lignocellulosic biomass as a carbon source. Moreover, the use of cellulosic biomass for production of bio-oil can overcome the factors limiting the development of bio-oil, including the unstable supply of food resources and an increase in the cost of raw materials, and can improve the commercial competitiveness of microbial fermentation oil. However, the effect of presence of toxic compounds in the pretreated biomass which are known to inhibitory to most of organisms was not studied.

WO 2007/068997 mentions the isolation and characterization of unreported 10 thraustochytrid strains from Goa, India for DHA production. Claimants screened these isolates on 2% glucose as carbon source to assess their ability for DHA accumulation and other related intermediate fatty acids. Authors claimed 10%-30% DHA content of total fatty acids in some of the isolates, however use of glucose as carbon source for DHA production raises serious question on the production cost along with long term supply of glucose for industrial scale DHA production when supply of cheap sources of glucose are already under pressure.

Patent publication number US2010/0041112 presents the application of lipid extracted from Thraustochytrid strains for biodiesel production. The strains used in this invention were extremely rich in SFA or MUFA. Use of glucose and yeast extract in the medium will translate into substantial escalation in production cost thus endangering the commercial viability of the process and long term sustainability both.

Addition of sea salt in the media is necessary for the Thraustochytrid cultivation however this may cause corrosion in large scale steal reactors and associated hardware thus to avoid this sea salt is replaced with non-chloride sodium salts such as sodium sulphate (US Pat. No. 5,340,742). However addition of non-chloride sodium salts in waste effluent stream will add further cost to the processing of waste streams. Therefore a process devoid of sea salt or sodium salt will be really helpful to integrate this process for processing of waste effluents From the prior art, it can concluded that use of other carbon sources other than glucose also poses the same question since long term supply of these carbon sources for large scale cultivation is questionable, if one is aiming for to use them as feedstock for biodiesel production. This will increase the carbon foot print of the process as well; an issue global community is grappling with. However integrating waste effluents processing with Thraustochytrid cultivation will add value to both the processes of waste effluents processing and biodiesel, DHA production from Thraustochytrid cultivation. This will in turn increase the commercial viability and sustainability of the process along with reducing carbon foot print of the process.

SUMMARY OF THE INVENTION

Accordingly the main embodiment of the present invention provides a process comprising two staged continuous fermentation for sequestration of nutrients from waste effluents of gas fermentation plants using Thraustochytrids for producing high value omega-3 fatty acids and lipids for biodiesel, said process comprising;
(a) culturing Thraustochytrids strains in a first stage fermentation rector comprising of waste effluent stream and nitrogen source;
(b) transferring the Thraustochytrids strains of step (a) through biomass harvesting system to second stage fermentation reactor having only waste effluent stream;
(c) culturing the biomass culture of step (b) in the second stage fermentation reactor optionally in absence of nitrogen;
(d) Separation of biomass and liquid broth and recycling of clear broth to gas fermentation plants; and
(e) obtaining value added omega-3 fatty acids and lipids.

Yet another embodiment of the present invention provides Use of novel strains of thraustochytrids having Accession No. MTCC 5890 (DBTIOC-1), MTCC 5895 (DBTIOC-6), MTCC 5893 (DBTIOC-14) and MTCC 5896 (DBTIOC-18) for producing omega-3 fatty acids and lipids for use in biodiesel.

Yet another embodiment of the present invention provides Novel strains of thraustochytrid having Accession No. MTCC 5890 (DBTIOC-1), MTCC 5895 (DBTIOC-6), MTCC 5893 (DBTIOC-14) and MTCC 5896 (DBTIOC-18).

Yet another embodiment of the present invention provides novel strains as herein described capable of producing omega-3 fatty acids and lipids for use in biodiesel.

Yet another embodiment of the present invention provides novel strains as herein described wherein the strains produce dry biomass in the range of 8 gm/litre/day to 150 gm/litre/day.

Yet another embodiment of the present invention provides novel strains as herein described wherein the strains produce lipids in the range of 20% of dry mass to 80% of dry mass.

Yet another embodiment of the present invention provides novel strains as herein described wherein the strains produce DHA content in the range of 15% of total fatty acid to 45% of fatty acid.

Another embodiment of the present invention provides a process as herein described, wherein waste effluents were containing mixture of organic acids and alcohol and no sugar or carbohydrate.

Another embodiment of the present invention provides a process as herein described, wherein the selected Thraustochytrid strains are MTCC 5890 (DBTIOC-1), MTCC 5895 (DBTIOC-6), MTCC 5893 (DBTIOC-14) and MTCC 5896 (DBTIOC-18).

Another embodiment of the present invention provides a process as herein described, wherein waste effluents contains acetate at a concentration of 5 g/L-100 g/L or more and alcohol at a concentration of 0.5 g/L or 5 g/L or more.

Another embodiment of the present invention provides a process as herein described, wherein omega-3 fatty acid fatty acids were palmitic acid, oleic acid, Docosahexaenoic acid (DHA), Docosapentaenoic acid (DPA), or Eicosapentaenoic acid (EPA).

Another embodiment of the present invention provides a process as herein described wherein in the absence of nitrogen increases the biomass in the range of 8 gm/litre/day to 100 gm/litre/day.

Another embodiment of the present invention provides a process as herein described wherein in the absence of nitrogen increases the lipid content in the range of 20% to 70% from the first stage fermentation reactor.

Another embodiment of the present invention provides a process as herein described wherein in the absence of nitrogen increases the DHA content is in the range of 15% of total fatty acid to 35% of total fatty acid from the first stage fermentation reactor.

Another embodiment of the present invention provides a process as herein described wherein the transfer of biomass directly from first reactor to second reactor enhance the dry biomass in the range of 8 gm/litre/day to 150 gm/litre/day.

Another embodiment of the present invention provides a process as herein described wherein the transfer of biomass directly from first reactor to second reactor enhance the lipid content in the range of 20% of dry mass to 80% of dry mass.

Another embodiment of the present invention provides a process as herein described wherein the transfer of biomass directly from first reactor to second reactor enhance the DHA content in the range of 15% of total fatty acid to 45% of fatty acid.

Another embodiment of the present invention provides a process as herein described wherein the removal of sulphide increased the biomass production in the range of 40 gm/litre/day to 55 gm/litre/day.

BRIEF DESCRIPTION OF THE FIGURES

FIG. 1. Strategy employed for the Thraustochytrid isolation.

FIG. 2. Phylogenetic relationship (NJ tree) of novel Thraustochytrid strains with existing Thraustochytrids FIG. 3(a). Acetate tolerance and biomass production on different concentration of acetate by Thraustochytrid strains FIG. 3(b). Acetate tolerance and lipid content on different concentration of acetate by Thraustochytrid strains FIG. 3(c). FAB and DHA content on different concentration of acetate by Thraustochytrid strains FIG. 4(a). Biomass production of Thraustochytrid strains on waste effluents FIG. 4(b). Lipid content of Thraustochytrid strains on waste effluents FIG. 4(c). FAB and DHA content of Thraustochytrid strains on waste effluents FIG. 5. Effect of addition of nitrogen source on biomass production on waste effluent stream FIG. 6. Effect of different inoculum sizes on biomass production on waste effluent stream FIG. 7(a). Cell count, Cell $OD_{600\ nm}$, dry biomass in bioreactor with combination of Rushton impeller and drilled pipe spargers for the cultivation of DBTIOC-18 (MTCC 5896) on waste effluent stream.

FIG. 7(b). Cell count, Cell $OD_{600\ nm}$, dry biomass in bioreactor with combination of pitch blade and microspargers for the cultivation of DBTIOC-18 (MTCC 5896) on waste effluent stream.

FIG. 8. Cell count, cell OD600 nm, cell size, dry biomass in 2 L bioreactor having 1.2 L working volume with combination of pitch blade and microspargers for the cultivation of DBTIOC-18 (MTCC 5896) on waste effluent stream continuously purged with air.

FIG. 9. Cell count, cell $OD_{600\ nm}$, cell size, dry biomass and lipid content in two stage bioreactor system having 1.2 L working volume, First reactor was continuously supplied with waste stream having nitrogen source whereas second reactor was supplied waste streams without amending with nitrogen source for the cultivation of DBTIOC-18 (MTCC 5896)

FIG. 10. Cell count, cell $OD_{600\ nm}$, cell size, dry biomass and lipid content in two stage bioreactor system with inline biomass harvesting system, First reactor was continuously supplied with waste stream having nitrogen source whereas second reactor was supplied waste streams without amending with nitrogen source for the cultivation of DBTIOC-18 (MTCC 5896). Biomass was continuously concentrated from broth coming out of first reactor and concentrated biomass was continuously pumped into second reactor.

FIG. 11. Schematic diagram of the process for the conversion of waste effluents to lipid and DHA

DETAILED DESCRIPTION

While the invention is susceptible to various modifications and/or alternative processes and/or compositions, specific embodiment thereof has been shown by way of example in the drawings, graphs and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims. Before the present methods and the products are described, it is to be understood that this invention is not limited to particular method, product and experimental conditions described; as such methods and conditions may vary. It is also to be understood that the terminology used herein is for purposes of describing particular embodiments only, and is not intended to be limiting.

The graphs, tables, figures and protocols have been represented where appropriate by conventional representations in the drawings, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other processes, sub-processes, composition, sub-compositions, minor or major compositions or other elements or other structures or additional processes or compositions or additional elements or additional features or additional characteristics or additional attributes.

The terms, "alone or in combination" or any other variations thereof, are intended to described and/or cover a non-exclusive inclusion, wherein the molecules or the oligonucleotides exist individually or together with any one or all of the other oligonucleotides.

Definitions

For the purposes of this invention, the following terms will have the meaning as specified therein:

As used herein, the terms "Two stage fermentation process" or "Two stage fermentation system" or "Two stage continuous fermentation process" or "Two stage continuous fermentation system" when used in the context of the present invention refers a process or method which comprises of two continuous fermentation reactions taking place in two separate reactors. The first fermentation takes place in the first stage fermentation reactor followed by second fermentation that takes place in the second stage fermentation reactor. Although both first and second fermentation reactions take place in separately in two different reactors but the overall process is continuous.

As used herein, the terms "Novel strains" when used in the context of the present invention refers to those strains that were created out of adaption of to extreme waste effluent streams of gas fermentation plants. The said "Novel Strains" are capable of multifold expression of multiple enzymes related for example Acetyl Co-A synthase, malic enzyme, ATP Citrate lyase, Isocitrate dehydrogenase etc. and capable of degrading high acetate containing waste effluents from gas fermentation plants.

As used herein, the terms "Omega-3 fatty acids" or "ω-3 fatty acids" or "n-3 fatty acids" refers to polyunsaturated fatty acids (PUFAs) with a double bond (C=C) at the third carbon atom from the end of the carbon chain. More specifically there are three types of Omega-3 fatty acids such as eicosapentaenoic acid (EPA), and docosahexaenoic acid (DHA) which have been considered, identified, studied and included as Omega-3 fatty acids in context of the present invention.

The present invention describes method and systems for continuous processing of waste effluents from gas fermentation or green-house gases managing plants for rapid conversion into omega-3 fatty acids and lipids using novel strains of Thraustochytrids. The novel strains of Thraustochytrid biomass is suitable feedstock for biodiesel production as well.

The present invention provides for novel wild strains of Thraustochytrid i.e. MTCC 5890 (DBTIOC-1), MTCC 5895 (DBTIOC-6), MTCC5893 (DBTIOC-14), MTCC 5896 (DBTIOC-18) that were isolation from mangrove ecosystem of the Indian coastline from degrading leaves or soil rich in dead organic matter from Mandovi Zuari mangroves, (Coordinates of Collection: S15°29'57.39",E73°52'6.13", Panjim, Goa) and identified and their characterization based on 18S rDNA gene sequencing was described. These 18S rDNA sequences have been deposited with NCBI database with accession Nos. KF668624, KF668627, KF668629 and KF668632.

In another aspect the present invention also provides for novel strains of thraustochytrid capable of expressing multifold expression of Acetyl Co-A synthase, malic enzyme, ATP Citrate lyase, Isocitrate dehydrogenase etc. and capable of degrading high acetate containing waste effluents from gas fermentation plants. Waste effluents discharged from gas fermentation plants also contained alcohol (0.5 g/L or 2 g/L or 5 g/L or more).

One aspect of the present invention provides for novel Thraustochytrid strains that are capable of hydrolyzing or degrading high acetate waste effluent. In one aspect the present invention provides for novel Thraustochytrid strains that can use acetate as carbon source present in the high acetate waste effluent in addition to yeast extract, peptones, corn steep liquor, nitrates, ammonium salts as nitrogen sources for the production of lipids and fatty acids.

In one aspect the present invention provides novel Thraustochytrid strains can tolerate wide range of acetate concentration from 5 g/L to 30 g/L to 50 g/L or more [FIG. 3 (a)-(c)]. In general the biomass was found in the range of 1.5 g/L to 6.5 g/L and lipid content was 14% to 54.5% w/w of biomass in the strains [FIG. 3 (a)-(c)]. For example the thraustochytrid strain MTCC 5896 (DBTIOC-18) has been found to utilize acetate in the range of 15 g/L which yielded 6.5 g/L biomass, 54.5% lipid and 15% DHA content.

Another aspect of the present invention provides for using effluent waste but not limited to the fermentation or greenhouse gases managing plants. In another aspect the present invention provides for novel Thraustochytrid strains as herein described which are capable of using both carbon and nitrogen source from various waste effluents. The nutrients in waste effluent or waste stream included organic acids and alcohol. The most common nutrients in the waste effluent/waste stream were found to be Acetic acid, formic acid and other acids along with alcohol. Thus with such a medium the biomass production was found to be ranging from 1.5 g/L to 3.3 g/L, lipid content was 21% to 50% of biomass and DHA content was 10% to 30% of total fatty acids (FIG. 4).

Another aspect of the present invention provides for the method of adapting the wild or parent strains to develop capability for hydrolyzing or degrading waste effluents. For adaptation of the wild or parent strains were cultured on waste effluents for longer duration for example one month, two month or three month or in some cases 6 months. Once nutrients are totally consumed in waste effluent streams, cultures were transferred to fresh stream. Transferring of culture was repeated 10 times, or 20 times, 30 times or in some cases 100 times. This enabled the wild or parent strains to selectively utilize nutrients from these streams and gradually adapt on waste effluents.

The novel strains showed higher nutrient sequestration i.e. 30 g/L, 50 g/L or 100 g/L from waste effluents and higher biomass and lipid production. These novel strains were able to tolerate very high concentration of organic acids particularly acetate/acetic acid and other growth inhibitors present in these streams. A Molecular analysis of the genes for example Acetyl Co-A synthase, malic enzyme, ATP Citrate lyase, Isocitrate dehydrogenase etc. associated with acetate metabolism showed multi fold increase in expression level in the novels strains compared to native strains.

In another aspect the novel strains were found to be efficient in respect of high robustness and productivity parameters such as biomass production, lipid content, TFA content, nutrient sequestration from stream remained higher as compare to native or control strains [(FIG. 4 (a)-(c) and (Table (1a)-(1b)]. These novel strains were later cultivated in Erlenmeyer flasks, baffle flasks or bioreactors.

TABLE 1(a)

Biomass production of different *Thraustochytrid* strains on waste effluents.

| Strains | Dry biomass (g/L) of novel strains on waste effluent | Dry biomass (g/L) of Control strains on waste effluent |
|---|---|---|
| MTCC5890 (DBTIOC-1) | 2.1-3.1 | 0.21-0.53 |
| MTCC 5895 (DBTIOC-6) | 2.4-3.3 | 0.23-0.61 |
| MTCC 5893 (DBTIOC-14) | 3.9-5.2 | 0.15-0.32 |
| MTCC 5896 (DBTIOC-18) | 2.5-3.4 | 0.25-0.61 |

TABLE 1(b)

Lipid content of different *Thraustochytrid* novel strains on waste effluents.

| Strains | Lipid content (%) of novel strains on waste effluent | Lipid content (%) of Control strains on waste effluent |
|---|---|---|
| MTCC5890 (DBTIOC-1) | 18-28 | 15-24 |
| MTCC 5895 (DBTIOC-6) | 28-35 | 19-32 |

TABLE 1(b)-continued

Lipid content of different *Thraustochytrid* novel strains on waste effluents.

| Strains | Lipid content (%) of novel strains on waste effluent | Lipid content (%) of Control strains on waste effluent |
|---|---|---|
| MTCC 5893 (DBTIOC-14) | 45-55 | 25-29 |
| MTCC 5896 (DBTIOC-18) | 35-46 | 25-30 |

In yet another aspect of the present invention it has been found that that novel thraustochytrid strains have unique and unexpected property of thriving both in presence and absence of nitrogen source. It was found in the present invention that lacking of adequate nitrogen supply triggered high lipid accumulation in the thraustochytrid strains. This enabled to adapt various strategies for use of novel thraustochytrid strains in production of biomass, lipid and DHA, for example amendment of waste effluent with nitrogen sources, increased inoculum size and adaptation of the selected strains on these waste effluents were applied to enhance biomass and lipid production. Moreover such a unique property of novel thraustochytrids enabled the applicants to develop and arrive at unique and novel method comprising of a two staged continuous fermentation for sequestration of nutrients from waste effluents of gas fermentation plants using Thraustochytrids for producing high value omega-3 fatty acids and lipids for biodiesel.

The various organic and inorganic nitrogen sources comprise of but are not limited to corn steep liquor, nitrates like sodium nitrate, potassium nitrates, ammonium nitrates, ammonium sulfate, ammonium chloride, and urea. The aforesaid nitrogen sources were added in the waste effluent medium. Thus in one aspect the present invention provides that the novel thraustochytrid strains when grown in medium comprising of waste effluent along with and nitrogen source resulted in higher growth of the novel thraustochytrid strains. Accordingly, in another aspect the of the present invention it was found that addition of sodium nitrate in the medium resulted into significant improvement in lipid content and lipid productivity in all the strains. Interestingly it was found that there was a two to three fold increase in the biomass concentration with the addition of nitrogen source [(FIG. 5) and (Table 2)]. For example in strain MTCC 5896 (DBTIOC-18) with addition of sodium nitrate in the effluent medium there was a two to three fold increase in the biomass concentration.

TABLE 2

Effect of addition of nitrogen source on biomass production on waste effluent stream

| Strains | Dry biomass (g/L) without nitrogen source | Dry biomass (g/L) with nitrogen source |
|---|---|---|
| MTCC5890 (DBTIOC-1) | 2.1-3.1 | 5.1-6.4 |
| MTCC 5895 (DBTIOC-6) | 2.4-3.3 | 3.2-5.5 |
| MTCC 5893 (DBTIOC-14) | 2.9-3.2 | 3.9-5.1 |
| MTCC 5896 (DBTIOC-18) | 2.5-3.4 | 6.1-7.3 |

A further aspect of the present invention provides that higher inoculum sizes for example 5%, 10%, 15%, 20% (v/v) was used to increase the removal of nutrients from waste effluents and increase the productivity of the process. Increase in inoculum sizes resulted into significant increase in biomass production with maximum reported almost 9 g/L with 20% v/v inoculum size (FIG. 6). All the nutrients (organic acids and alcohols) were totally removed from the stream.

In another aspect the present invention it has been found that the need of adding sea salt or equivalent (such as sea water) was not required for the processing of waste effluents by novel strains. These strains were able to actively grow without the addition of sea salt or equivalent in the stream and producing almost equal biomass and lipid content. This was significant improvement in the process since this will not only avoid corrosion of steal fermenters but also extra cost associated with replacement of sea salt with other non-chloride sodium salts. This also underlines the fact that avoiding addition of sea salt in the media will not increase the salinity of effluent stream thus this stream water was recycled for gas fermentation.

In another aspect the present invention provides for novel thraustochytrid strains that were able to tolerate increase in pH for example up to 9 or 9.5 without compromising the nutrient sequestration rate and productivity of the process thus reducing the need of pH balance during the cultivation of strains which will further reduce the cost associated with processing of waste effluents.

In another aspect the present invention also provides for a reactor system comprising of reactor impellers that could prevent damage to delicate cells under lipid accumulation stage by shear force. Accordingly, on aspect of the present invention the large scale cell lysis was observed during lipid accumulation phase. Thus to avoid this different type of impellers for example Rushton, pitch blade or marine impellers were used. It was observed that use of pitch blade impeller significantly reduce the cell lysis during lipid accumulation phase thus enhancing the number of active cells present in the vessel. This in turn translated into faster nutrient sequestration from waste effluent streams and prevented loss of products such as lipid and DHA.

In another aspect of the present invention the reactor was run in batch, fed batch, semi continuous and continuous mode. To make reactor continuous, effluent was continuously pumped in with one tube while culture was simultaneously removed from other overflow tube installed in the reactor Nitrogen source was supplied continuously or intermittently along with effluent stream. Sometimes effluent stream was supplied without addition of nitrogen source.

In another aspect the present invention also provide another unique design in the reactor system wherein the reactor was fitted with microspargers instead of drilled pipe spargers. Combination of different types of spargers and impellers were applied to enhance masse transfer rate, biomass, lipid and DHA productivity and simultaneously decreasing agitation rate, shearing and power consumption. Combination of microspargers with pitch blade resulted into faster nutrient sequestration rate, higher biomass production rate. Combination of microspargers and pitch blade impeller improved nutrient sequestration from 2 grams/litre/day to 18 grams/litre/day to 30 grams/litre/day or 55 grams/litre/day more from waste streams, which resulted into higher biomass production from 0.5 grams/litre/day to 4.8 grams/litre/day to 8 grams/litre/day or 40 grams/litre/day more [FIGS. 7(*a*)-(*b*)].

In another aspect of the present invention during high density culture, excessive foam was being generated, which was controlled by either continuous or intermittent addition of antifoam in the reactor. Sometimes antifoam negatively affected the growth and biomass production rate. Most of the antifoam tested, was found negatively affecting the growth and biomass production.

In another aspect the black coloured waste effluent coming from gas fermentation plants was continuously purged with air to remove traces of sulphides which gives black colour to the effluent, which later fed into the reactor. Sometimes purging effluent stream with air resulted into higher nutrient sequestration rate and biomass production rate. This resulted into further increase in nutrient sequestration from 55 g/L/d to 90 g/L/d or more and biomass production from 40 g/L/d to 55 g/L/d or more. However comparing to batch or fed batch, lipid content decreased from 55% of dry biomass or 70% or more of dry biomass to 20% or 30% or more of dry biomass (FIG. 8).

In another aspect of the present invention the supply of nitrogen source was stopped to increase lipid content of the cell, whereas in other case nitrogen source was continuously supplied to support growth. Continuous supply of nitrogen source resulted into reduced lipid production but higher growth. To support lipid production along with growth, two reactor systems was set up. One reactor was designated to promote growth while another for lipid accumulation in the cell. First reactor is kept at high aeration rate to maintain higher dissolve oxygen whereas second reactor is kept at low dissolve oxygen level.

In another aspect of the present invention the culture coming out from first reactor was directly transferred into second reactor to induce lipid production under nitrogen stress. First reactor was continuously supplied with effluent stream containing nitrogen source whereas second reactor was supplied with effluent stream only. Culture coming out of second reactor showed improved biomass and lipid production. Biomass increased from 8 g/L/d to 30 g/L/d or 65 g/L/d or 95 g/L/d or 100 g/L/d or more, whereas lipid content increased from 20% of dry biomass to 40% or 50% or 60% or 70% or more of dry biomass. DHA production also improved from 15% of total fatty acid to 25% or 30% or 35% of total fatty acids (FIG. 9).

In another aspect of the present invention a biomass separating system was installed between two reactors for continuous separation of cells and broth to transfer concentrated biomass to second reactor to induce lipid accumulation in the cell.

In yet another aspect of the present invention the culture broth coming out from first reactor was continuously passed through biomass separating system, where cells are concentrated and transferred to second reactor. In second reactor residence time for cells are higher to promote lipid accumulation in the cell under low dissolve oxygen level and deplete the oxygen completely from the broth. Dry biomass increased from 8 g/L/d to 30 g/L/d or 65 g/L/d or 95 g/L/d or 150 g/L/d or more, whereas lipid content increased from 20% of dry biomass to 40% or 50% or 60% or 80% or more of dry biomass. DHA production also improved from 15% of total fatty acid to 25% or 30% or 45% or more of total fatty acids (FIG. 10).

In yet another aspect of the present invention the alcohols particularly ethanol present in waste effluent stream caused increment in DHA production in the biomass. DHA content increased from 15% of total fatty acid to 25% or 30% or 45% or more of total fatty acids. Doping of waste effluent stream with ethanol resulted into further rise in DHA production in the biomass from 15% of total fatty acid to 25% or 30% or 45% or 50% or more of total fatty acids.

In yet another aspect of the present invention the second reactor was installed with overflow tube for the continuous harvesting of the lipid rich biomass. Culture coming out of second reactor was continuously passed through second biomass separating system to separate out biomass and broth. This broth was totally devoid of oxygen therefore this broth was totally or partly recycled back for the gas fermentation process.

In yet another aspect of the present invention the broth water, continuously separated out from the biomass, was recycled back for gas fermentation process thus drastically reducing the need of water for whole process. Sometimes broth water was purged with nitrogen to flush out oxygen from it (FIG. 11).

In yet another aspect of the present invention one or two or three or more novel strains of thraustochytrids were co-cultivated to enhance nutrient sequestration rate, biomass, lipid and DHA productivity. In another aspect the present invention provides one or more novel strains alone or in combination to enhance nutrient sequestration rate, biomass, lipid and DHA productivity. In another aspect the present invention provides a single strain to enhance nutrient sequestration rate, biomass, lipid and DHA productivity. In another aspect the present invention provides two or more novel strains alone or combination to enhance nutrient sequestration rate, biomass, lipid and DHA productivity.

Another aspect of the present invention provides for a process that was developed in way to synchronize it with any gas fermentation process to produce high value coproduct from green-house gases at significantly higher rate than conventional phototrophic algae driven green-house gas sequestration process. A person skilled in art understands that waste effluents from other sources, rich in organic acids/alcohols/sugars can be used for nutrients sequestration using this process.

Accordingly the main embodiment of the present invention provides a process comprising two staged continuous fermentation for sequestration of nutrients from waste effluents of gas fermentation plants using Thraustochytrids for producing high value omega-3 fatty acids and lipids for biodiesel, said process comprising;
(a) culturing Thraustochytrids strains in a first stage fermentation rector comprising of waste effluent stream and nitrogen source;
(b) transferring the Thraustochytrids strains of step (a) through biomass harvesting system to second stage fermentation reactor having only waste effluent stream;
(c) culturing the biomass culture of step (b) in the second stage fermentation reactor optionally in absence of nitrogen;
(d) Separation of biomass and liquid broth and recycling of clear broth to gas fermentation plants; and
(e) obtaining value added omega-3 fatty acids and lipids.

Another embodiment of the present invention provides a process as herein described, wherein waste effluents were containing mixture of organic acids and alcohol and no sugar or carbohydrate.

Another embodiment of the present invention provides a process as herein described, wherein the selected Thraustochytrid strains are MTCC 5890 (DBTIOC-1), MTCC 5895 (DBTIOC-6), MTCC 5893 (DBTIOC-14) and MTCC 5896 (DBTIOC-18).

Another embodiment of the present invention provides a process as herein described, wherein waste effluents contains acetate at a concentration of 5 g/L-100 g/L or more and alcohol at a concentration of 0.5 g/L or 5 g/L or more.

Another embodiment of the present invention provides a process as herein described, wherein omega-3 fatty acid fatty acids were palmitic acid, oleic acid, Docosahexaenoic acid (DHA), Docosapentaenoic acid (DPA), or Eicosapentaenoic acid (EPA).

Another embodiment of the present invention provides a process as herein described, wherein the step 1(b), the culture from first fermentation reactor was directly transferred into the second fermentation reactor.

Another embodiment of the present invention provides a process as herein described, wherein the step 1(c) culture of second fermentation reactor was cultured in absence of nitrogen.

Another embodiment of the present invention provides for a process as herein described, wherein in the absence of nitrogen increases the biomass in the range of 8 gm/litre/day to 150 gm/litre/day, preferably in the range of 8 gm/litre/day to 100 gm/litre/day.

Another embodiment of the present invention provides for a process as herein described, wherein in the absence of nitrogen increases the lipid content in the range of 20% to 90% from the first stage fermentation reactor, preferably in the range of 20% to 70% from the first stage fermentation reactor.

Another embodiment of the present invention provides for a process as herein described, wherein in the absence of nitrogen increases the DHA content in the range of 15% of total fatty acid to 50% of total fatty acid from the first stage fermentation reactor, preferably in the range 15% of total fatty acid to 35% of total fatty acid from the first stage fermentation reactor.

Another embodiment of the present invention provides for a process as herein described wherein the transfer of biomass directly from first reactor to second reactor enhance the dry biomass in the range of 8 gm/litre/day to 200 gm/litre/day, preferably in the range of 8 gm/litre/day to 150 gm/litre/day Another embodiment of the present invention provides for a process as herein described wherein the transfer of biomass directly from first reactor to second reactor enhance the lipid content in the range of 20% of dry mass to 100% of dry mass, preferably in the range of 20% of dry mass to 80% of dry mass.

Another embodiment of the present invention provides for a process as herein described wherein the transfer of biomass directly from first reactor to second reactor enhance the DHA content in the range of 15% of total fatty acid to 50% of fatty acid, preferably enhance the DHA content in the range of 15% of total fatty acid to 45% of fatty acid.

Another embodiment of the present invention provides for a process as herein described wherein the removal of sulphide increased the in nutrient sequestration in the range of 55 gm/litre/day to 90 gm/litre/day, preferably in the range of 40 gm/litre/day to 55 gm/litre/day.

Another embodiment of the present invention provides for a process as herein described, wherein the strains produce (a) dry biomass in the range of 8 gm/litre/day to 150 gm/litre/day; (b) lipids in the range of 20% of dry mass to 80% of dry mass; and (c) DHA content in the range of 15% of total fatty acid to 45% of fatty acid.

Another embodiment of the present invention provides a process as herein described wherein in the absence of nitrogen increases the biomass in the range of 8 gm/litre/day to 150 gm/litre/day.

Another embodiment of the present invention provides a process as herein described wherein in the absence of nitrogen increases the biomass in the range of 8 gm/litre/day to 100 gm/litre/day.

Another embodiment of the present invention provides a process as herein described wherein in the absence of nitrogen increases the lipid content in the range of 20% to 90% from the first stage fermentation reactor.

Another embodiment of the present invention provides a process as herein described wherein in the absence of nitrogen increases the lipid content in the range of 20% to 70% from the first stage fermentation reactor.

Another embodiment of the present invention provides a process as herein described wherein in the absence of nitrogen increases the DHA content in the range of 15% of total fatty acid to 50% of total fatty acid from the first stage fermentation reactor.

Another embodiment of the present invention provides a process as herein described wherein in the absence of nitrogen increases the DHA content is in the range of 15% of total fatty acid to 35% of total fatty acid from the first stage fermentation reactor.

Another embodiment of the present invention provides a process as herein described wherein the culture from the first stage fermentation reactor was continuously passed through biomass separating reactor to separate out biomass and broth.

Another embodiment of the present invention provides a process as herein described wherein the concentrated biomass obtained from separating system was continuously transferred to second stage fermentation reactor.

Another embodiment of the present invention provides a process as herein described wherein the transfer of biomass directly from first reactor to second reactor enhance the dry biomass in the range of 8 gm/litre/day to 200 gm/litre/day.

Another embodiment of the present invention provides a process as herein described wherein the transfer of biomass directly from first reactor to second reactor enhance the dry biomass in the range of 8 gm/litre/day to 150 gm/litre/day.

Another embodiment of the present invention provides a process as herein described wherein the transfer of biomass directly from first reactor to second reactor enhance the lipid content in the range of 20% of dry mass to 100% of dry mass.

Another embodiment of the present invention provides a process as herein described wherein the transfer of biomass directly from first reactor to second reactor enhance the lipid content in the range of 20% of dry mass to 80% of dry mass.

Another embodiment of the present invention provides a process as herein described wherein the transfer of biomass directly from first reactor to second reactor enhance the DHA content in the range of 15% of total fatty acid to 50% of fatty acid.

Another embodiment of the present invention provides a process as herein described wherein the transfer of biomass directly from first reactor to second reactor enhance the DHA content in the range of 15% of total fatty acid to 45% of fatty acid.

Another embodiment of the present invention provides a process as herein described wherein the second reactor was used to create continuous nitrogen stress condition to stimulate lipid accumulation in the cell.

Another embodiment of the present invention provides a process as herein described wherein the culture coming out of second fermentation reactor was continuously passed through biomass separating system to separate out biomass and broth water and wherein the water was having zero dissolved oxygen was continuously recycled back for gas fermentation process.

Another embodiment of the present invention provides a process as herein described wherein the waste effluent was continuously purged with air to remove traces of sulphide.

Another embodiment of the present invention provides a process as herein described wherein the removal of sulphide increased the in nutrient sequestration in the range of 55 gm/litre/day to 90 gm/litre/day.

Another embodiment of the present invention provides a process as herein described wherein the removal of sulphide increased the biomass production in the range of 40 gm/litre/day to 55 gm/litre/day.

Yet another embodiment of the present invention provides Novel strains of thraustochytrid having Accession No. MTCC 5890 (DBTIOC-1), MTCC 5895 (DBTIOC-6), MTCC 5893 (DBTIOC-14) and MTCC 5896 (DBTIOC-18).

Yet another embodiment of the present invention provides novel strains as herein described capable of producing omega-3 fatty acids and lipids for use in biodiesel.

Yet another embodiment of the present invention provides novel strains as herein described wherein the strains produce dry biomass in the range of 8 gm/litre/day to 150 gm/litre/day.

Yet another embodiment of the present invention provides novel strains as herein described wherein the strains produce lipids in the range of 20% of dry mass to 80% of dry mass.

Yet another embodiment of the present invention provides novel strains as herein described wherein the strains produce DHA content in the range of 15% of total fatty acid to 45% of fatty acid.

Yet another embodiment of the present invention provides Use of novel strains of thraustochytrids having Accession No. MTCC 5890 (DBTIOC-1), MTCC 5895 (DBTIOC-6), MTCC 5893 (DBTIOC-14) and MTCC 5896 (DBTIOC-18) for producing omega-3 fatty acids and lipids for use in biodiesel.

One embodiment of the present invention provides a process as herein described wherein the novel strains are able to produce lipid content in the range of 14% to 54.5% w/w of biomass in the strains.

In another embodiment the present invention provides a thraustochytrid strain MTCC 5896 (DBTIOC-18) capable of utilizing or reducing acetate to yield 6.5 g/L biomass, 54.5% lipid and 15% DHA content.

Another embodiment of the present invention provides a process as herein described wherein the biomass production is in the range of 1.5 g/L to 3.3 g/L, lipid content is in the range of 21% to 50% of biomass and DHA content is in the range of 10% to 30% of total fatty acids (FIG. 4).

Another embodiment of the present invention provides thraustochytrid strains having Accession No. MTCC 5890 (DBTIOC-1), MTCC 5895 (DBTIOC-6), MTCC 5893 (DBTIOC-14) and MTCC 5896 (DBTIOC-18) wherein the strains show multi fold increase in the expression of Acetyl Co-A synthase, malic enzyme, ATP Citrate lyase, Isocitrate dehydrogenase etc.

Another embodiment of the present invention provides thraustochytrid strains having Accession No. MTCC 5890 (DBTIOC-1), MTCC 5895 (DBTIOC-6), MTCC 5893 (DBTIOC-14) and MTCC 5896 (DBTIOC-18) wherein the strains show multi fold increase in the expression of enzymes associated with acetate metabolism, wherein the enzyme may be selected from group of one or more Acetyl Co-A synthase, malic enzyme, ATP Citrate lyase, Isocitrate dehydrogenase etc.

Another embodiment of the present invention provides thraustochytrid strains having Accession No. MTCC 5890 (DBTIOC-1), MTCC 5895 (DBTIOC-6), MTCC 5893 (DBTIOC-14) and MTCC 5896 (DBTIOC-18) wherein the strains show multi fold increase in the expression of enzymes selected from group of one or more Acetyl Co-A synthase, malic enzyme, ATP Citrate lyase, Isocitrate dehydrogenase etc, wherein the multi fold expression of the said enzymes may be alone or in combination with each other.

Another embodiment of the present invention provides novel strains as herein described highly efficient in respect of high robustness and productivity parameters such as biomass production, lipid content, TFA content and nutrient sequestration Yet another embodiment of the present invention provides novel strains as herein described are capable of producing biomass in the range of 2 g/L to 6 g/L, preferably 2.1-5.2 g/L [Table 1(a)].

Another embodiment of the present invention provides novel strains as herein described capable of producing biomass in the range of 2.1 to 3.1 g/l, 2.4 to 3.3 g/l, 3.9 to 5.2 g/l or/and 2.5 to 3.4 g/l [Table 1(a)].

Yet another embodiment of the present invention provides novel strains as herein described are capable of producing lipid content in the range of 18% to 60%, preferably 18%-55% [Table 1(b)].

Another embodiment of the present invention provides novel strains as herein described are capable of producing lipid content in the range of 18% to 28%, 28% to 35%, 45% to 55% 1 or/and 35% to 46% [Table 1(b)].

Yet another embodiment of the present invention provides a process as herein described wherein the biomass production is in the range of 2 g/L to 6 g/L, preferably 2.1-5.2 g/L.

Another embodiment of the present invention provides a process as herein described wherein the biomass is in the range of 2.1 to 3.1 g/l, 2.4 to 3.3 g/l, 3.9 to 5.2 g/l or/and 2.5 to 3.4 g/l [Table 1(a)].

Yet another embodiment of the present invention provides a process as herein described wherein the lipid content is in the range of 18% to 60%, preferably 18%-55% [Table 1(b)].

Another embodiment of the present invention provides a process as herein described wherein the lipid content is in the range of 18% to 28%, 28% to 35%, 45% to 55% 1 or/and 35% to 46% [Table 1(b)].

Yet another embodiment of the present invention provides novel strains as herein described which enhance the biomass by two to three folds with addition of nitrogen source.

Yet another embodiment of the present invention provides novel strains as herein described wherein addition of nitrogen source enhances the biomass in the average range of 3-8 g/l [Table 2].

Yet another embodiment of the present invention provides novel strains as herein described wherein addition of nitrogen source enhances the biomass in the range of 3.3-5.5 g/l, 3.9-5.1 g/l, 5.1-6.4 g/l and/or 6.1-7.3 g/l [Table 2].

Yet another embodiment of the present invention provides a nitrogen source as herein described selected from any of the known conventional naturally occurring or artificial known nitrogen sources.

Yet another embodiment of the present invention provides a process as herein described wherein there is two to three fold increases in the biomass with addition of nitrogen source.

Yet another embodiment of the present invention provides a process as herein described wherein addition of nitrogen source enhances the biomass in the average range of 3-8 g/l [Table 2].

Yet another embodiment of the present invention provides a process as herein described wherein addition of nitrogen source enhances the biomass in the range of 3.3-5.5 g/l, 3.9-5.1 g/l, 5.1-6.4 g/l and/or 6.1-7.3 g/l [Table 2].

In another embodiment the present invention provides a process as herein described wherein biomass production is increased is upto 9 g/L (FIG. 6).

In another embodiment the present invention provides novel strains as herein described wherein the strains are capable of producing biomass upto 9 g/L (FIG. 6).

Another embodiment of the present invention provides a process as herein described wherein the combination of microspargers and pitch blade impeller enhanced nutrient sequestration from 2 gm/litre/day to 55 gm/litre/day, which resulted in increase in biomass in the range of 0.5 gm/litre/day to 40 gms/litre/day [FIGS. 7(*a*)-(*b*)].

Another embodiment of the present invention provides a process as herein described wherein the combination of microspargers and pitch blade impeller enhanced the in the range of 2 gm/litre/day to 18 gm/litre/day to 30 gm/litre/day or 55 gm/litre/day, which resulted in increase of biomass in the range of 0.5 gm/litre/day to 4.8 grams/litre/day to 8 grams/litre/day or 40 grams/litre/day more [FIGS. 7(*a*)-(*b*)].

In another embodiment the present invention provides a process as herein described wherein the removal of sulphides increased the in nutrient sequestration in the range of 55 gm/litre/day to 90 gm/litre/day.

In another embodiment the present invention provides a process as herein described wherein the removal of sulphides increased the biomass production in the range of 40 gm/litre/day to 55 gm/litre/day. (FIG. 8).

In another embodiment the present invention provides a process as herein described wherein supply of nitrogen to only first reactor and absence of nitrogen in the second reactor resulted in increase of biomass in the range of 8 gm/litre/day to 150 gm/litre/day (FIG. 9).

In another embodiment the present invention provides a process as herein described wherein supply of nitrogen to only first reactor and absence of nitrogen in the second reactor resulted in increase of biomass in the range of 8 gm/litre/day to 30 gm/litre/day or 65 gm/litre/day or 95 gm/litre/day or 100 gm/litre/day (FIG. 9).

In another embodiment the present invention provides a process as herein described wherein supply of nitrogen to only first reactor and absence of nitrogen in the second reactor resulted in increase of lipid content in the range of 20% of dry biomass to 90% of dry biomass (FIG. 9).

In another embodiment the present invention provides a process as herein described wherein supply of nitrogen to only first reactor and absence of nitrogen in the second reactor resulted in increase of lipid content in the range of 20% of dry biomass to 40% or 50% or 60% or 70% or more of dry biomass (FIG. 9).

In another embodiment the present invention provides a process as herein described wherein supply of nitrogen to only first reactor and absence of nitrogen in the second reactor resulted in increase in DHA in the range of 15% of total fatty acid to 50% of total fatty acids (FIG. 9).

In another embodiment the present invention provides a process as herein described wherein supply of nitrogen to only first reactor and absence of nitrogen in the second reactor resulted in increase in DHA in the range of 15% of total fatty acid to 25% or 30% or 35% of total fatty acids (FIG. 9).

In another embodiment of the present provides a process as herein described wherein the cell culture of the first reactor was concentration and then transferred to the second reactor thereby increasing the dry biomass in the range of 8 gm/litre/day to 200 gm/litre/day (FIG. 10).

In another embodiment of the present provides a process as herein described wherein the cell culture of the first reactor was concentration and then transferred to the second reactor thereby increasing the dry biomass in the range of 8 gm/litre/day to 30 gm/litre/day or 65 gm/litre/day or 95 gm/litre/day or 150 gm/litre/day (FIG. 10).

In another embodiment of the present invention provides a process as herein described wherein the cell culture of the first reactor was concentration and then transferred to the second reactor thereby increasing the lipid content in the range of 20% of dry biomass to 100% of dry biomass (FIG. 10).

In another embodiment of the present provides a process as herein described wherein the cell culture of the first reactor was concentration and then transferred to the second reactor thereby increasing the lipid content in range of 20% of dry biomass to 40% or 50% or 60% or 80% or more of dry biomass (FIG. 10).

In another embodiment of the present provides a process as herein described wherein the cell culture of the first reactor was concentration and then transferred to the second reactor thereby increasing the DHA production in the range of 15% of total fatty acid to 50% of total fatty acids (FIG. 10).

In another embodiment of the present provides a process as herein described wherein the cell culture of the first reactor was concentration and then transferred to the second reactor thereby increasing the DHA production in the range of 15% of total fatty acid to 25% or 30% or 45% or more of total fatty acids (FIG. 10).

Another embodiment of the present invention provides for use of novel strains of thraustochytrids as herein described for the process of production of biofuels.

Another embodiment of the present invention provides for use of novel strains of thraustochytrids as herein described for the process of production of (a) biomass in the range of 8 gm/litre/day to 150 gm/litre/day, preferably in the range of 8 gm/litre/day to 100 gm/litre/day; (b) increases the lipid content in the range of 20% to 90% from the first stage fermentation reactor, preferably in the range of 20% to 70% from the first stage fermentation reactor; and (c) DHA content in the range of 15% of total fatty acid to 50% of total fatty acid from the first stage fermentation reactor, preferably in the range 15% of total fatty acid to 35% of total fatty acid from the first stage fermentation reactor.

Another embodiment of the present invention provides for use of novel strains of thraustochytrids as herein described for the process of production of (a) dry biomass in the range of 8 gm/litre/day to 200 gm/litre/day, preferably in the range of 8 gm/litre/day to 150 gm/litre/day; (b) lipid content in the range of 20% of dry mass to 100% of dry mass, preferably in the range of 20% of dry mass to 80% of dry mass; and (c) DHA content in the range of 15% of total fatty acid to 50% of fatty acid, preferably enhance the DHA content in the range of 15% of total fatty acid to 45% of fatty acid.

Another embodiment of the present invention provides a process as herein described wherein in the absence of nitrogen increases the (a) biomass in the range of 8 gm/litre/day to 150 gm/litre/day, preferably in the range of 8 gm/litre/day to 100 gm/litre/day; (b) increases the lipid content in the range of 20% to 90% from the first stage fermentation reactor, preferably in the range of 20% to 70% from the first stage fermentation reactor; and (c) DHA content in the range of 15% of total fatty acid to 50% of total fatty acid from the first stage fermentation reactor, preferably in the range 15% of total fatty acid to 35% of total fatty acid from the first stage fermentation reactor.

The following description is of exemplary embodiments only and is not intended to limit the scope, applicability or configuration to the invention in any way. Rather, the following description provides a convenient illustration for implementing exemplary embodiments of the invention various changes to the described embodiments may be made in the functions and arrangement of the elements described without departing from the scope of the invention.

EXAMPLES

Example 1

Isolation of Thraustochytrids from Indian Marine Biodiversity

Large number of samples (Soil, water, degraded leaves etc) was collected from Indian marine sites in March 2013 over 30-35 km stretch in mangrove areas of Ribandar across Mandovi-Zuari mangroves (Collection Coordinates: S15°29'57.39",E73°52'6.13", Panjim Goa). Physical parameters such as geographic position, pH, temperature and humidity of the collection site were recorded with GPS, pH meter, thermometer and hygroscope respectively. 100 μl of selective antibiotic mixture was added into each falcon and samples were stored in dry ice packs and brought to lab along with natural sea water within 24 hours for processing. Direct plating or baiting method were the two protocols followed for the isolation. Soil samples were diluted 1000 times or leaf samples were washed, with sterile sea water before spreading on agar plates. Water samples were directly spread on agar plates. These agar plates were supplemented with selective antibiotic mixture. All the samples were baited with sterile pine pollens or other selected material (25-30 mg) and incubated at 25° C. for 8-10 days until colonization appears on the periphery of pollens. Colonization was checked daily after 5 days under light microscope. Once pollens are colonized, 100 μl of the water was taken from surface of falcon carefully and spread on antibiotic containing agar plates. Media for these plates were containing glucose (10 g/L), Yeast extract (1 g/L), peptone (1 g/L), agar (10 g/L) filtered natural sea water (100% v/v) and antibiotic mixture. These plates were incubated at 25° C. for 7-10 days. Colonies appeared on the plates were observed under microscope (40×) for morphological study. Thraustochytrid like colonies were picked up and further streaked on agar plates having above described media composition with 70% Natural sea water. Thraustochytrid like strains were purified after 3-4 streaking on agar plates having selected antibiotic mixture. Presence of Omega-3 fatty acids particularly DHA is one of the key parameters for quick identification of Thraustochytrids (FIG. 1). Therefore lipids from the biomass of all the strains were extracted and converted in to fatty acid methyl esters by adopting known methods. These FAMEs were analyzed by GC-FID especially for presence of DHA.

Example 2

Molecular Characterization of Isolated Thraustochytrid Strains

For genetic identification of the strains, 1 ml of 5 day old culture was harvested and genomic DNA was extracted according to the guidelines described in DNeasy blood and tissue kit (Qiagen, USA). Genomic DNA was used for PCR amplification of 18S rRNA gene using primers T18S1F 5'-CAACCTGGTTGATCCTGCCAGTA-3' and T18S5R 5'-TCACTACGGAAACCTTGTTACGAC-3' (Honda et al. 1999). 25 μL PCR reaction was setup having 12.5 μL PCR master mix (Applied Biosystem, USA), 0.5 μL each primer (T18S1F, T18S5R), 1 μL genomic DNA, 10.5 μL milliQ water. PCR program included 3 min at 94° C. for initial denaturation, 45 sec at 94° C. for final denaturation, 30 sec at 64° C. for annealing, 2 min at 72° C. for extension, 10 min at 72° C. (final extension) for 30 cycles. PCR product was purified from 1% agarose gel using QiAquick gel extraction kit (Qiagen, USA) and mixture for PCR product and primers was sent to Macrogen (South Korea) for sequencing. The resulting 18S rRNA gene sequence was compared with known Thraustochytrids 18S rRNA gene sequences in NCBI gene bank database using basic local alignment search tool (BLAST). strains sequence along with other known sequences of Thraustochytrids were used to construct phylogenetic tree (NJ tree) using MEGA 6 software (FIG. 2). The resulting sequences were deposited in NCBI database (with accession no. KF668624, KF668627, KF668629, KF668632). Strains i.e. MTCC 5890 (DBTIOC-1), MTCC 5895 (DBTIOC-6), MTCC 5893 (DBTIOC-14), MTCC 5896 (DBTIOC-18) were deposited at Microbial Type Culture Collection and Gene Bank (MTCC) Institute of Microbial Technology (IMTECH), Chandigarh, India Example 3

Screening of Thraustochytrid Strains for their Ability to Acetate Utilization and Acetate Tolerance Different concentration of acetate such as 5 g/L, 30 g/L, 50 g/L or 100 g/L were added in the nutrient rich medium as sole carbon source or mixed with other carbon sources. pH of acetic acid was raised to 7 with sodium hydroxide followed by addition of 10 g/L yeast extract, 1 g/L peptone. 18 g/L artificial sea salt was added in the medium to mimic 50% strength of sea water. Residual acetate was measure by HPLC and it was found that maximum acetate utilization does not go beyond 15 g/L in shake flask culture. However strain tolerance towards higher concentration of acetate was tested up to 50 g/L or 100 g/L. Strain DBTIOC-18 (MTCC 5896) performed better on acetate as carbon as compare to other strains irrespective of amount of acetate in the medium (FIG. 3).

Example 4

Screening of Thraustochytrid Strains for Nutrient Sequestration from Waste Effluents Waste effluents used in this invention were discharged from gas fermentation of green-houses gases or from deacetylation of lignocellulosic biomass or pyrolysis of lignocellulosic biomass or refining of crude oil etc. Chemical composition of these effluents revealed the dominant presence organic acids (particularly acetic acid, propionic acid, butyric acid) along with other acids and alcohols such as ethanol (0.5 g/L or 2 g/L 5 g/L or more) in the stream. This stream was as such autoclaved at 121° C. for 20 minutes without any additional nutrient source including nitrogen sources. 50 ml culture in 250 ml flask was harvested after 5 day and biomass was dried overnight. Lipids were extracted and FAMEs ware analyzed with the given method. In control strains biomass was ranging from 0.17 g/L to 0.61 g/L with slow nutrient sequestration (FIG. 4). Different strategies such as adaptation of strains on waste streams, addition of nitrogen sources and higher inoculum size were applied to increase the nutrient sequestration rate from waste streams.

For adaptation the strains were cultured on waste effluents for longer duration for example one month, two month or three month or in some cases 6 months. Once nutrients are totally consumed in waste effluent streams, cultures were transferred to fresh stream. Transferring of culture was repeated 10 times, or 20 times, 30 times or in some cases 100 times. This enabled the strains to selectively utilize nutrients from these streams and gradually adapt on waste effluents resulting into higher biomass production (FIG. 4). Moreover the effect of the nitrogen source was also studied on the novel strains wherein addition of nitrogen source in waste effluents stream significantly increased nutrient sequestration and biomass production. The analysis of the biomass and the lipids showed that the novel strains were efficient in the production of the high biomass and lipids (FIG. 5). Addition of different inoculum sizes i.e. 5%, 10%, 15% and 20% also helped to increase nutrient sequestration and biomass production using waste streams as nutrient media without supplementing any nitrogen source (FIG. 6).

Examples 5

Different Continuous Cultivation Methods for the Cultivation of Selected Strain on Waste Effluent in Bioreactor Inoculum of selected strains of thraustochytrid was prepared in YPD media having 30 g/L glucose, 10 g/L yeast extract, 1 g/L peptone and 18 g/L sea salt and incubated at 25° C., 150 rpm. 10% of 48 h old inoculum was added in 2 L or 7 L or 14 L reactors, half filled with waste effluents having nitrogen source. Culture was aerated with normal drilled pipe spargers or microspargers or other type of microspargers whereas culture was agitated with Rushton or pitch blade or marine impeller or other impellers at 100 rpm or 200 rpm or 300 rpm or more. Dissolve oxygen was maintained at 10% or 20% or 30% or 50% or more with combination of air and oxygen supply. Sample was taken regularly at the interval of 8 to 12 h to determine nutrient sequestration, biomass production, lipid content and DHA production. Acetate consumption measurement was used as marker for the measurement of nutrient sequestration from waste effluents. Reactor pH was maintained at 7 with acid and base. In fed batch cultivation, waste effluents augmented with organic acids and alcohol were directly fed to culture.

In continuous mode of cultivation two tubes were installed in the reactor, one tube for continuous addition of waste effluent with or without nitrogen source whereas overflow tube was installed for continuous harvesting the culture (FIG. 7).

In two stage reactor system, broth coming out of first reactor is directly pumped into second reactor. First reactor was continuously supplied with nitrogen and high aeration whereas second reactor was not supplied with any nitrogen source and with very low dissolve oxygen. This system helped to increase lipid content particularly DHA by many fold.

In two stage reactor system with biomass separating system, a biomass harvesting system is installed between first and second reactor and another is installed after second reactor to separate biomass from liquid broth. Broth coming out from first reactor goes to biomass harvesting system where biomass is concentrated and pumped into second reactor. Obsessed cells coming out from second reactor is continuously transferred to another biomass separating system where biomass is separated out from liquid broth. This clear liquid broth is continuously purged with nitrogen and supplied back to gas fermentation reactors (FIG. 11).

Example 6

Lipid Extraction and Fatty Acid Analysis

For lipid extraction definite amount of dried biomass was taken and lipid was extracted with modified Bligh and Dyer method (FIGS. 3 and 4). For FAME analysis, 500 µl toluene was added in dried lipid extract followed by 100 µl internal standard (methyl tricosanoate C19:0) and 100 µl butylated hydroxytoluene (BHT). Acidic methanol (400 µl) was added into tube and kept for 10-12 hours at 50° C. 1 ml of 5% NaCl was added followed by the addition of 1 ml hexane and upper layer was transferred into fresh tube. FAMEs were washed with 1 ml of 2% Potassium bicarbonate and moisture was removed by passing it through anhydrous sodium sulphates. FAMEs were concentrated under nitrogen and analyzed with GC-FID system (Perkin Elmer clarus680, US), equipped with fast-GC capillary column (Omegawax100, 15 m×0.1 mm, 0.1 µm thickness). 1 µl of FAMEs were injected at injector temperature 250° C. Oven temperature was started increasing from initial 140° C. to final 280° C. with ramping rate of 40° C./sec and hold for 2 min. Detector was set at 260° C. Hydrogen was used as carrier gas with velocity rate 50 cm sec-1. Fatty acid peaks were identified and quantified with Totalchrome chromatography software (Perkin Elmer, US).

We claim:

1. A process comprising two staged continuous fermentation for sequestration of nutrients from waste effluents of gas fermentation plants using Thraustochytrids for producing high value omega-3 fatty acids and lipids for biodiesel, said process comprising;
   (a) Continuous culturing Thraustochytrid strains in a first stage fermentation reactor comprising continuous supply of waste effluent stream and nitrogen source;
   (b) Continuous transferring the culture of Thraustochytrid strains of step (a) through biomass harvesting/separator system to a second stage fermentation reactor having only waste effluent stream;
   (c) Continuous culturing the biomass of step (b) producing a concentrated biomass in the second stage fermentation reactor optionally in absence of nitrogen;
   (d) Continuous separating of the biomass from broth through biomass harvesting/separator system; and recycling of the broth to gas fermentation plants; and
   (e) obtaining omega-3 fatty acids and lipids for biodiesel wherein the Thraustochytrid strains are selected from the group consisting of strain MTCC 5890 (DBTIOC-1), strain MTCC 5895 (DBTIOC-6), strain MTCC 5893 (DBTIOC -14) and strain MTCC 5896 (DBTIOC-18).

2. The process as claimed in claim 1, wherein waste effluents were containing mixture of organic acids and alcohol, sulphides and no sugar or carbohydrate.

3. The process as claimed in claim 1, wherein waste effluents contains acetate at a concentration of 5g/L-100g/L or more and alcohol at a concentration of 0.5 g/L or 5 g/L or more.

4. The process as claimed in claim 1, wherein omega-3 fatty acid fatty acids were Docosahexaenoic acid (DHA), Docosapentaenoic acid (DPA), or Eicosapentaenoic acid (EPA).

5. The process as claimed in claim 1, wherein step (b), the culture from first fermentation reactor was directly transferred into the second fermentation reactor.

6. The process as claimed in claim 1, wherein step (c), the culture of second fermentation reactor was cultured in absence of nitrogen.

7. The process as claimed in claim 1, wherein in the absence of nitrogen, the biomass increases in the range of 8 gm/liter/day to 150 gm/liter/day.

8. The process as claimed in claim 1, wherein in the absence of nitrogen, the lipid content increases in the range of 20% to 90% from the first stage fermentation reactor.

9. The process as claimed in claim 1, wherein in the absence of nitrogen, the DHA content increases in the range of 15% of total fatty acid to 50% of total fatty acid from the first stage fermentation reactor.

10. The process as claimed in claim 1, wherein step (b) culture from the first stage fermentation reactor was continuously passed through biomass separating reactor to separate out biomass and broth.

11. The process as claimed in claim 5, wherein the transfer of biomass directly from first reactor to second reactor enhance the dry biomass in the range of 8 gm/liter/day to 200 gm/liter/day.

12. The process as claimed in claim 1, wherein the transfer of biomass directly from first reactor to second reactor enhance the lipid content in the range of 20% of dry mass to 80% of dry mass.

13. The process as claimed in claim 1, wherein the transfer of biomass directly from first reactor to second reactor enhance the DHA content in the range of 15% of total fatty acid to 50% of fatty acid.

14. The process as claimed in claim 1, wherein in step 1 (c) absence of nitrogen in the second reactor creates a continuous nitrogen stress condition to stimulate lipid accumulation in the cell.

15. The process as claimed in claim 1, wherein the broth coming out of second reactor was having zero dissolved oxygen and recycled back to gas fermenting plants.

16. The process as claimed in claim 2, wherein step 1 (a) the waste effluent was continuously purged with air to oxidize sulphides.

17. The process as claimed in claim 2, wherein the sulphides from the waste effluents increased the nutrient sequestration in the range of 55 gm/liter/day to 90 gm/liter/day.

* * * * *